US010485416B2

(12) United States Patent
Ng

(10) Patent No.: US 10,485,416 B2
(45) Date of Patent: Nov. 26, 2019

(54) OCULAR MODELING METHODS AND APPARATUS

(71) Applicant: Novartis AG, Basel (CH)

(72) Inventor: Eugene Ng, Dublin (IE)

(73) Assignee: Novartis AG, Basel (CH)

( * ) Notice: Subject to any disclaimer, the term of this patent is extended or adjusted under 35 U.S.C. 154(b) by 169 days.

(21) Appl. No.: 15/831,775

(22) Filed: Dec. 5, 2017

(65) Prior Publication Data
US 2018/0092524 A1 Apr. 5, 2018

Related U.S. Application Data

(63) Continuation of application No. 14/945,657, filed on Nov. 19, 2015, now abandoned, which is a continuation of application No. 13/138,772, filed as application No. PCT/EP2010/054051 on Mar. 26, 2010, now Pat. No. 9,220,404.

(60) Provisional application No. 61/172,673, filed on Apr. 24, 2009, provisional application No. 61/163,806, filed on Mar. 26, 2009.

(51) Int. Cl.
A61B 3/00 (2006.01)
A61B 3/18 (2006.01)
A61F 2/16 (2006.01)
G09B 23/30 (2006.01)

(52) U.S. Cl.
CPC ............ A61B 3/0025 (2013.01); A61B 3/18 (2013.01); A61F 2/16 (2013.01); G09B 23/30 (2013.01); A61F 2240/002 (2013.01)

(58) Field of Classification Search
CPC ......... A61B 3/0025; A61B 3/18; A61B 3/185; A61B 3/10; A61B 3/1005; A61B 3/1015; A61B 3/102; A61B 3/103; A61B 3/107; A61B 3/117; A61B 3/1173; A61B 3/1176
See application file for complete search history.

(56) References Cited

U.S. PATENT DOCUMENTS

| 4,632,528 | A | * | 12/1986 | Yoshino | ............... | A61B 3/1005 351/211 |
| 7,237,898 | B1 | * | 7/2007 | Hohla | ................ | A61F 9/00806 351/246 |
| 2003/0038920 | A1 | * | 2/2003 | Lin | ........................ | A61F 9/007 351/212 |
| 2004/0066489 | A1 | * | 4/2004 | Benedikt | ................ | A61B 3/102 351/212 |
| 2009/0164007 | A1 | * | 6/2009 | Van Heugten | ....... | A61B 3/1005 623/6.11 |

* cited by examiner

Primary Examiner — Cara E Rakowski

(57) ABSTRACT

A method and apparatus for modelling a lens (104) of an eye (100), comprising: measuring (302) the anterior shape of the eye's cornea (102); determining (304) direct optical measurements of at least one parameter of the cornea (102) of the eye (100) and at least one parameter of the lens (104) of the eye (100); determining (306) the refractive index of the cornea; correcting (308) the optical measurements to account for the effect of the refractive index of the cornea on the direct optical measurements; measuring (310) the aberration of the eye; calculating (312) the refractive index of the lens by combining the corrected measurements and the aberration; and further correcting (314) the optical measurements of the lens to account the effect of the refractive index of the lens on the direct optical measurements.

16 Claims, 10 Drawing Sheets

OCULAR MODELING METHODS AND APPARATUS

CLAIM OF PRIORITY

This application is a continuation of U.S. application Ser. No. 14/945,657, filed on Nov. 19, 2015, which claims the benefit of priority under 35 U.S.C. § 365 of International Patent Application Serial No. PCT/EP2010/054051 filed on Mar. 26, 2010, designating the United States of America, which in turn claims the benefit of priority of U.S. Provisional Patent Application 61/163,806, filed on Mar. 26, 2009 and U.S. Provisional Patent Application 61/172,673, filed on Apr. 24, 2009, which PCT Application and U.S. Provisional Patent Applications are incorporated by reference herein.

FIELD OF THE INVENTION

The technology described herein relates to ocular modeling.

BACKGROUND TO THE INVENTION

Ocular procedures often modify one or more structures of the eye, such as the cornea, lens, or retina. Some procedures involve removing or replacing one or more structures of the eye, or adding an implant. For example, lens replacement surgery involves removing a patient's existing lens and replacing it with a new lens. Some procedures, such as laser vision correction surgery, do not remove or replace existing structures of patient's eye, or add an implant to the eye, but rather re-shape existing structures. Regardless of the type of modification being made (e.g., removal, replacement, insertion, or alteration), the optical performance of the eye is altered by the alteration of the structures of the eye.

SUMMARY OF THE INVENTION

According to some aspects of the technology described herein with reference to the appended claims, apparatus and methods are described to facilitate modeling of one or more structures of an eye. The structures may be the cornea, the lens, or any other structures of the eye.

According to the present invention there is provided a method of modelling a lens of an eye, the method comprising: measuring the anterior shape of the eye's cornea; determining direct optical measurements of at least one parameter of the cornea of the eye and at least one parameter of the lens of the eye; determining the refractive index of the cornea; correcting the optical measurements to account for the effect of the refractive index of the cornea on the direct optical measurements; measuring the aberration of the eye; calculating the refractive index of the lens by combining the corrected measurements and the aberration; and further correcting the optical measurements of the lens to account the effect of the refractive index of the lens on the direct optical measurements. The direct optical measurements may be made using topography or interferometry.

Preferably, the at least one parameter of the cornea of the eye comprises at least one of cornea thickness, posterior cornea shape and distance from the back of the cornea to the front of the lens and the at least one parameter of the lens of the eye comprises at least one of anterior lens shape, posterior lens shape, lens thickness and distance from back of lens to the retina. The refractive index (index of refraction) of the cornea may be determined using a refractometer.

Preferably, the refractive index of the cornea is determined by combining direct optical measurements of the cornea of the eye. The aberration may be measured using a refractometer. The refractive index of the lens may be calculated by matching a composite refractive index of the lens, and optical measurements of the lens to a total composite refraction or total composite aberrometry from the eye.

The direct optical measurements may further comprise measurements of the total ocular refraction and aberration in the absence of the lens, the total volume of aqueous; or total refraction and aberration with fluid in the lens capsule and anterior chamber. The direct optical measurements may further comprise a distance from the back of the cornea to the retina of the eye, the distance measured in the absence of the lens of the eye. The direct optical measurements may further comprise a volume of aqueous. The direct optical measurements may further comprise the aberration of the eye and a distance from the back of the cornea to the retina in the absence of the lens of the eye measured with fluid in the lens capsule and anterior chamber.

The refractive index of the cornea, the refractive index of the lens and the anterior and posterior shape of the cornea and the lens may be measured using a laser array source comprising one or more lasers. Measuring the anterior shape of the eye's cornea may comprise: capturing one or more images of a pattern of laser spots generated on the anterior surface of the cornea by the laser array source; forming an averaged image from the captured images; and comparing the averaged images to spacing and arrangement of the lasers of the laser array source.

Measuring the posterior shape of the cornea of the eye may comprise: capturing one or more images of a pattern of laser spots generated on the posterior surface of the cornea by the laser array source; forming an averaged image from the captured images; and comparing the averaged images to spacing and arrangement of the lasers of the laser array source.

Computing the anterior lens shape may comprise: capturing one or more images of a pattern of laser spots generated on the anterior surface of the lens by the laser array source; forming an averaged image from the captured images; and comparing the averaged images to spacing and arrangement of the lasers of the laser array source.

Computing the posterior lens shape may comprise: capturing one or more images of a pattern of laser spots generated on the posterior surface of the lens by the laser array source; forming an averaged image from the captured images; and comparing the averaged images to spacing and arrangement of the lasers of the laser array source. The refractive index of the lens may be determined using a difference image determined using the reflection of one laser spot appearing on the anterior of the lens and the corresponding spot appearing on the posterior of the lens.

The present invention further provides a method of determining an optimum position for a replacement intraocular lens based on the effective position of the natural lens, said natural lens having an anterior surface and a posterior surface, the method comprising modelling the anterior and posterior surfaces of the natural lens using the method of modelling a lens of an eye as set out above; extrapolating the anterior and posterior surfaces to cross points; and determining the optimum position to line in the place joining said cross points.

The present invention further provides an alternative method of determining an optimum position for a replacement intraocular lens based on the effective position of the natural lens, said natural lens having an anterior surface and a posterior surface, the method comprising: modelling the anterior and posterior surfaces of the natural lens using the method of modelling a lens of an eye as set out above; determining the diameter of the natural lens; extrapolating the anterior and posterior lens surfaces to the diameter; determining the arc length of the natural lens using said diameter; and determining the optimum position to lie at the midpoint of the arc length.

The present invention further provides a further alternative method of determining an optimum position for a replacement intraocular lens based on the effective position of the natural lens, said natural lens having an anterior surface and a posterior surface, the method comprising: approximating a best fit curve for the posterior surface using the anterior lens surface, lens thickness and a historical ratio between the anterior and posterior lens curvatures.

According to the present invention there is also provided an apparatus for modelling a lens of an eye, the apparatus comprising: means for measuring the anterior shape of the eye's cornea; means for determining direct optical measurements of at least one parameter of the cornea of the eye and at least one parameter of the lens of the eye; means for determining the refractive index of the cornea; means for correcting the optical measurements to account for the effect of the refractive index of the cornea on the direct optical measurements; means for measuring the aberration of the eye; means for calculating the refractive index of the lens by combining the corrected measurements and the aberration; and means for further correcting the optical measurements of the lens to account the effect of the refractive index of the lens on the direct optical measurements.

The means for determining the direct optical measurements may utilize topography or interferometery. The at least one parameter of the cornea of the eye may comprise at least one of cornea thickness, posterior cornea shape and distance from the back of the cornea to the front of the lens and wherein the at least one parameter of the lens of the eye may comprise at least one of anterior lens shape, posterior lens shape, lens thickness and distance from back of lens to the retina. The means for determining the refractive index of the cornea may comprise a refractometer. The means for determining the refractive index of the cornea may comprise means for combining the direct optical measurements of the cornea of the eye. The means for measuring the aberration of the eye may comprise a refractometer. The means for calculating the refractive index of the lens may be adapted to match a composite refractive index of the lens, and optical measurements of the lens, to a total composite refraction or total composite aberrometry from the eye. The direct optical measurements may further comprise measurements of the total ocular refraction and aberration in the absence of the lens, the total volume of aqueous; or total refraction and aberration with fluid in the lens capsule and anterior chamber. The direct optical measurements may further comprise a distance from the back of the cornea to the retina of the eye, the distance measured in the absence of the lens of the eye. The direct optical measurements may further comprise a volume of aqueous. The direct optical measurements may further comprise the aberration of the eye and a distance from the back of the cornea to the retina in the absence of the lens of the eye measured with fluid in the lens capsule and anterior chamber.

The means for measuring the refractive index of the cornea, the refractive index of the lens and the anterior and posterior shape of the cornea and the lens may comprises a laser array source comprising one or more lasers.

The means for measuring the anterior shape of the eye's cornea may comprise: means for capturing one or more images of a pattern of laser spots generated on the anterior surface of the cornea by the laser array source; means for forming an averaged image from the captured images; and means for comparing the averaged image to spacing and arrangement of the lasers of the laser array source. The means for measuring the posterior shape of the cornea of the eye may comprise: means for capturing one or more images of a pattern of laser spots generated on the posterior surface of the cornea by the laser array source; means for forming an averaged image from the captured images; and means for comparing the averaged image to spacing and arrangement of the lasers of the laser array source. The means for computing the anterior lens shape may comprise: means for capturing one or more images of a pattern of laser spots generated on the anterior surface of the lens by the laser array source; means for forming an averaged image from the captured images; and means for comparing the averaged image to spacing and arrangement of the lasers of the laser array source. The means for computing the posterior lens shape may comprise: means for capturing one or more images of a pattern of laser spots generated on the posterior surface of the lens by the laser array source; means for forming an averaged image from the captured images; and means for comparing the averaged image to spacing and arrangement of the lasers of the laser array source.

The means for determining the refractive index of the lens may be adapted to use a difference image determined using the reflection of one laser spot appearing on the anterior of the lens and the corresponding spot appearing on the posterior of the lens.

The present invention further provides an apparatus for determining an optimum position for a replacement intraocular lens based on the effective position of the natural lens, said natural lens having an anterior surface and a posterior surface, the apparatus comprising: means for modelling the anterior and posterior surfaces of the natural lens using the apparatus for modelling a lens of an eye of the present invention as set out above; means for extrapolating the anterior and posterior surfaces to cross points; and means for determining the optimum position to line in the place joining said cross points.

The present invention further provides an apparatus for determining an optimum position for a replacement intraocular lens based on the effective position of the natural lens, said natural lens having an anterior surface and a posterior surface, the apparatus comprising: means for modelling the anterior and posterior surfaces of the natural lens using the apparatus for modelling a lens of an eye of the present invention as set out above; means for determining the diameter of the natural lens; means for extrapolating the anterior and posterior lens surfaces to the diameter; means for determining the arc length of the natural lens using said diameter; and means for determining the optimum position to lie at the midpoint of the arc length.

The present invention further provides an apparatus of determining an optimum position for a replacement intraocular lens based on the effective position of the natural lens, said natural lens having an anterior surface and a posterior surface; the apparatus comprising: means for modelling the anterior and posterior surfaces of the natural lens using the apparatus for modelling a lens of an eye of the present invention as set out above; and means for approximating a best fit curve for the posterior surface using the anterior lens surface, lens thickness and a historical ratio between the anterior and posterior lens curvatures. According to one aspect of the present invention, a method of determining intraocular lens position is provided. The method comprises determining, using an interferometer, a first distance from an anterior surface of a cornea to an anterior surface of the lens. The method further comprises correcting the first distance to account for an refractive index of the cornea to produce a second distance. The method further comprises determining, using the interferometer, a third distance from the anterior surface of the lens to a posterior surface of the lens. The method further comprises correcting the third distance to account for an refractive index of the lens.

According to another aspect of the invention, a method is provided comprising projecting an array of laser beams toward an ocular surface using a laser array source, thereby producing a pattern of laser spots on the ocular surface. The method further comprises determining, at least partially from the pattern of laser spots, an optical parameter of the ocular surface or an ocular material.

According to another aspect of the present invention, an apparatus is provided, comprising a laser array source for producing a plurality of laser beams, the laser array source configured to project the plurality of laser beams onto a surface, the plurality of laser beams creating a pattern of laser spots on the surface. The apparatus further comprises a first imaging device and a second imaging device configured to capture images of the pattern of laser spots. The first imaging device and the second imaging device are positioned approximately symmetrically about the plurality of laser beams.

The present invention further provides at least one computer-readable storage medium encoded with instructions that, when executed, perform a method of determining, at least partially from a pattern of laser spots on an ocular surface, an optical parameter of the ocular surface or an ocular material.

Accordingly, the present invention provides a method of determining the three dimensional position and/or geometry of the natural lens and lens equator using direct or indirect measurements. The direct measurements may be used if the natural lens equator is accessible by either optical or ultrasound methods and indirect measurements if natural lens equator is not accessible by similar methods and correcting any measurements for distortion as a result of different speed of light and sound in different medium for example refractive index in the case of optical methods and speed of sound in the case of ultrasound methods. Any indirect measurements, for example, may include the measurement, computation and/or historical correlation of anterior lens curvature, posterior lens curvature, lens thickness and/or lens diameter to the three dimensional position or geometry of natural lens equator. Any measurements using light methods may include using any combinations and permutations of light technology including but not exclusively Purkinje imaging, Scheimpflug imaging, interferometry, optical coherence tomography, aberrometry and/or refractometry.

It will be appreciated that position may be determined by measuring, either before or during surgery. These measurements may include a first distance from anterior surface of cornea to posterior surface of cornea; a second distance from posterior surface of cornea to anterior surface of lens; a third distance from anterior surface of lens to posterior surface of lens; a fourth distance from posterior surface of lens to anterior surface of retina and a fifth distance from anterior surface of retina to posterior surface of retina.

When determining geometry, measurements including a first curvature of anterior surface of cornea; a second curvature of posterior surface of cornea; a third curvature of anterior surface of lens; a fourth curvature of posterior surface of lens; and a fifth curvature of anterior surface of retina; a sixth curvature of posterior surface of retina may be taken.

It will be appreciated that these measurements will vary due to optical abberations. The present invention may also include correcting for distortions of any/all measurements and may include using historical averages or computing for speed of sound or refractive index using at least one of the methods described above.

It will be appreciated that the present invention provides a method of determining three dimensional intraocular lens position either before or during surgery and any combination and permutation of the embodiments described. According to one embodiment, the method may comprise extrapolating the anterior and posterior surfaces to cross points and determining the optimum position to line in the place joining said cross points in a second embodiment, determining the diameter of the natural lens and extrapolating the anterior and posterior lens surfaces to the diameter, hence determining the arc length of the natural lens using said diameter so as to determine the optimum position to lie at the midpoint of the arc length in a third embodiment, approximating a best fit curve for the posterior surface using the anterior lens surface, lens thickness, a historical ratio between the anterior and posterior lens curvatures and/or the diameter of the natural lens.

Determining the diameter of the natural lens may be performed before surgery and/or by injection of a fixed volume of fluid during surgery. Determining the posterior curvature of the lens and/or the distance from the posterior surface of the cornea to the posterior surface of the lens may be performed before surgery specifically after removal of the lens for example, if the lens is optically opaque.

It will be appreciated that the present invention may incorporate altering predicted retinal image and may comprise some or all of the optical methods described above; in addition to calculating coordinates of light (image) source; calculating coordinates of light source at each ocular surface as it travel through successive interface; calculating coordinates at which light source arrives at the posterior surface of the retina in relation to the centre of the retina (fovea); altering any permutation and combination of refractive index, distance and/or curvature of lenses or any ocular surfaces to achieve a desired retinal image.

As used herein, the optical parameter may be a shape of the ocular surface. The optical parameter may also be the distance from one ocular surface to another. The optical parameter may be an refractive index of the ocular material. The ocular surface may be a first ocular surface. Altering predicted retinal image may also comprise: focusing the array of laser beams approximately to a point on a second ocular surface while the pattern of laser spots is formed on the first ocular surface. The method may also comprise capturing a first image of the pattern of laser spots with a first imaging device and capturing a second image of the pattern of laser spots with a second imaging device The method may also comprise producing a combined image combining the first image and the second image. Determining, at least partially from the pattern of laser spots, an optical parameter, may comprise determining the optical parameter at least partially from the combined image. The combined image may be an average of the first image and the second image, and wherein the optical parameter may be a shape of the ocular surface. The combined image may be a difference of the first image and the second image, and wherein the optical parameter is an refractive index of the ocular material. The first imaging device and the second imaging device may be positioned approximately symmetrically about the array of laser beams.

The apparatus of the present invention may further comprise at least one processor configured to receive output signals from the first imaging device and the second imaging device, and to process the output signals to form a combined image representing a combination of a first image of the pattern of laser spots captured by the first imaging device and a second image of the pattern of laser spots captured by the second imaging device.

The at least one processor may comprise a first processor configured to receive output signals from the first imaging device and a second processor configured to receive output signals from the second imaging device, the first processor and second processor being communicatively coupled to form the combined image.

The surface may be a first ocular surface, and the apparatus may further comprise an interferometer configured to determine a distance from the first ocular surface to a second ocular surface. The first and second ocular surfaces may be part of an eye, and wherein the apparatus may further comprise a beam splitter positioned between the laser array source and the eye and also between the interferometer and the eye. The interferometer may be a single wavelength low or partial coherence interferometer. The first imaging device and the second imaging device may be fixed in place while capturing images of the plurality of laser spots. The first imaging device may be a CCD camera.

There is also provided a computer program comprising program instructions for causing a computer program to carry out the above method which may be embodied on a record medium, carrier signal or read-only memory.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should accorded a meaning most consistent with the particular concepts disclosed herein.

BRIEF DESCRIPTION OF THE DRAWINGS

Various non-limiting embodiments of the technology described herein will now be described with specific reference to the following figures. It should be appreciated that the figures are not necessarily drawn to scale.

DETAILED DESCRIPTION OF THE DRAWINGS

Apparatus and methods for modeling one or more structures of the eye are described. The modeling may indicate the shape and/or location of the structures of the eye, which may be determined using optical methods for determining one or more parameters of the ocular structure of interest, as well as of the structures preceding the ocular structure of interest. The one or more parameters may include shape, thickness, and refractive index.

The measurement of any one of shape, thickness and/or refractive index of an ocular structure of interest may depend to some extent on the directional changes which light employed by the measurement technique undergoes while passing through any ocular structures preceding the structure of interest. Thus, according to one aspect of the technology, measurements of shape, thickness, and/or refractive index of ocular structures may be corrected to account for the dependence of the measured values on the other parameters for that structure, as well as on any of the parameters of preceding structures.

According to another aspect, apparatus are provided for measuring the shape, thickness, and refractive index of ocular structures of interest. According to one embodiment, the apparatus includes distinct instruments for measuring one or more of the parameters of interest. According to another embodiment, an apparatus includes integrated functionality for measuring the parameters of interest. According to one non-limiting embodiment, the apparatus includes a laser array which projects a plurality of laser beams onto an ocular structure of interest, thus forming a laser spot pattern. The distances between the laser spots of the laser spot pattern may be used to calculate one or more parameters of the structure, such as the shape and refractive index. According to some embodiments, the apparatus also determines the thickness of structures of an eye using interferometry.

The aspects of the technology mentioned above, as well as additional aspects, will now be described in greater detail. These aspects may be used individually, all together, or in any combination of two or more, as the technology is not limited in this respect.

As mentioned, according to one aspect of the technology described herein, the shapes and locations of ocular structures may be determined, from which an accurate model of the eye may be made. The structures may include the cornea, the lens, the retina, or any other structures of interest. The shape and location of a structure may be determined by direct measurement of one or more parameters, including shape, thickness, and refractive index, and then correction of any measurements to account for dependence on other parameters of the measured structure or on any parameters of other structures within the eye. An example is now described in connection with FIG. 1.

Figure 1:
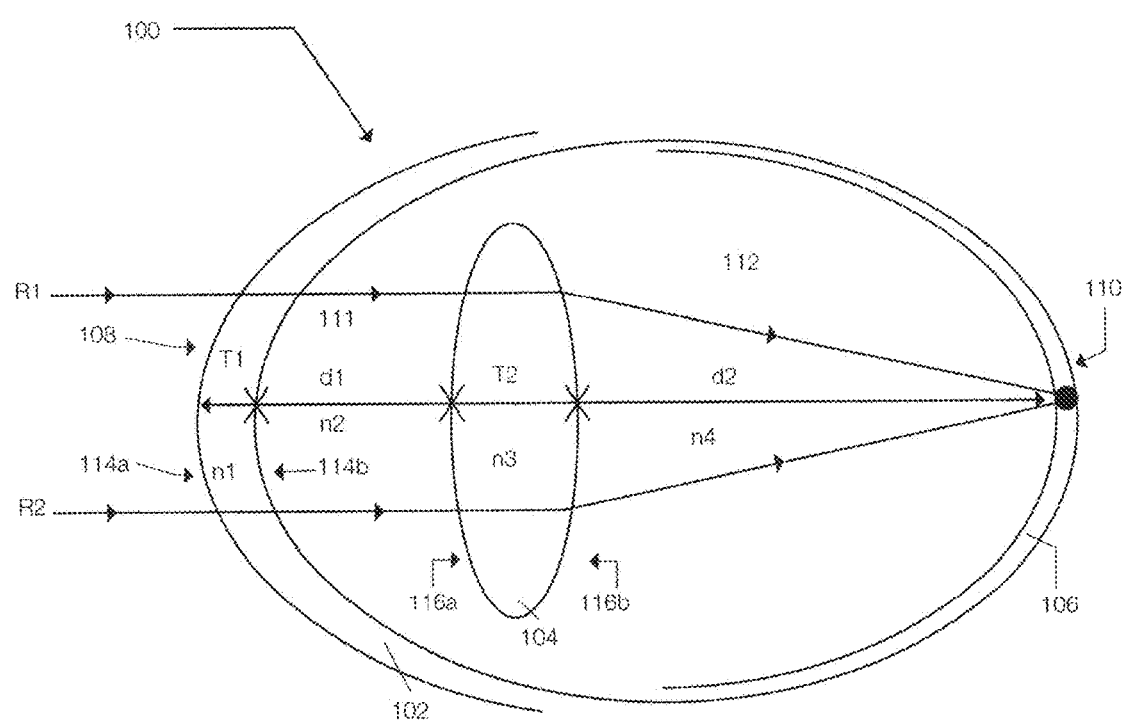
FIG. 1 is a simplified schematic of an eye.

FIG. 1 provides a simplified representation of an eye 100, including a cornea 102, a lens 104, and a retina 106. These structures are arranged between a front side 108 of the eye, where light enters, and a back side 110 of the eye. Between the cornea 102 and the lens 104 is a volume of aqueous 111. Between the lens 104 and the retina 106 is a volume of vitreous gel 112. It should be appreciated that the eye 100 is simplified for purposes of illustration, and that eyes typically include more features than those shown in FIG. 1.

As mentioned, modeling the eye 100 may involve determining the shape of one or more surfaces of interest, such as the front surface 114a of the cornea, the back surface 114b of the cornea, etc. Topography, for example Scheimpflug topography, is one technique that may be used to determine the shapes of such surfaces. However, other methods, including Purkinje imaging, interferometry and/or optical coherence tomography may also be used.

As also mentioned, modeling the eye 100 to provide locations of the ocular structures may involve determining various distances within the eye. As shown, the cornea 102 has a thickness T1, between the front surface 114a of the cornea and the back surface 114b of the cornea, and lens 104 has a thickness T2, between the front surface 116a of the lens and the back surface 116b of the lens. The cornea and lens are separated by a distance d1 (i.e., the distance from the back surface 114b of the cornea and the front surface 116a of the lens). The retina is separated from the back surface 116b of the lens by a distance d2. Such distances may be measured using interferometry, or other techniques, as the various aspects described herein are not limited in this respect.

However, while topography and interferometry techniques may be used to measure shapes and distances of ocular structures, such direct measurement techniques alone may not produce entirely accurate results. The light employed by such measurement techniques may undergo directional changes induced by the varying indices of refraction of the ocular structures (i.e., refractive index n1 of the cornea, refractive index n2 of the aqueous, refractive index n3 of the lens, and refractive index n4 of the vitreous gel), such that the results may not be accurate if not accounting for such directional changes. The concept is explained with reference to FIG. 1.

As shown, the rays R1 and R2, which may correspond to the light sources employed in conventional topography and/or interferometry techniques, originate on the front side 108 of the eye 100, and terminate on the retina 106. They do not follow a straight path, but rather are bent as they pass through the cornea 102, the aqueous 111, the lens 104, and the vitreous gel 112. The illustrated paths of rays R1 and R2 are simplified for purposes of explanation, and may be different in practice, either involving more or fewer changes in direction than those shown, and changes of different direction than those shown.

The directional changes of light employed by measurement techniques such as topography and interferometry may thus influence the results of such measurements. Applicant has appreciated that such direct optical measurements of shape and thickness may be corrected for their dependence on the path of light within the eye, to enable highly accurate determination of shapes and locations of ocular structures.

Figure 2:
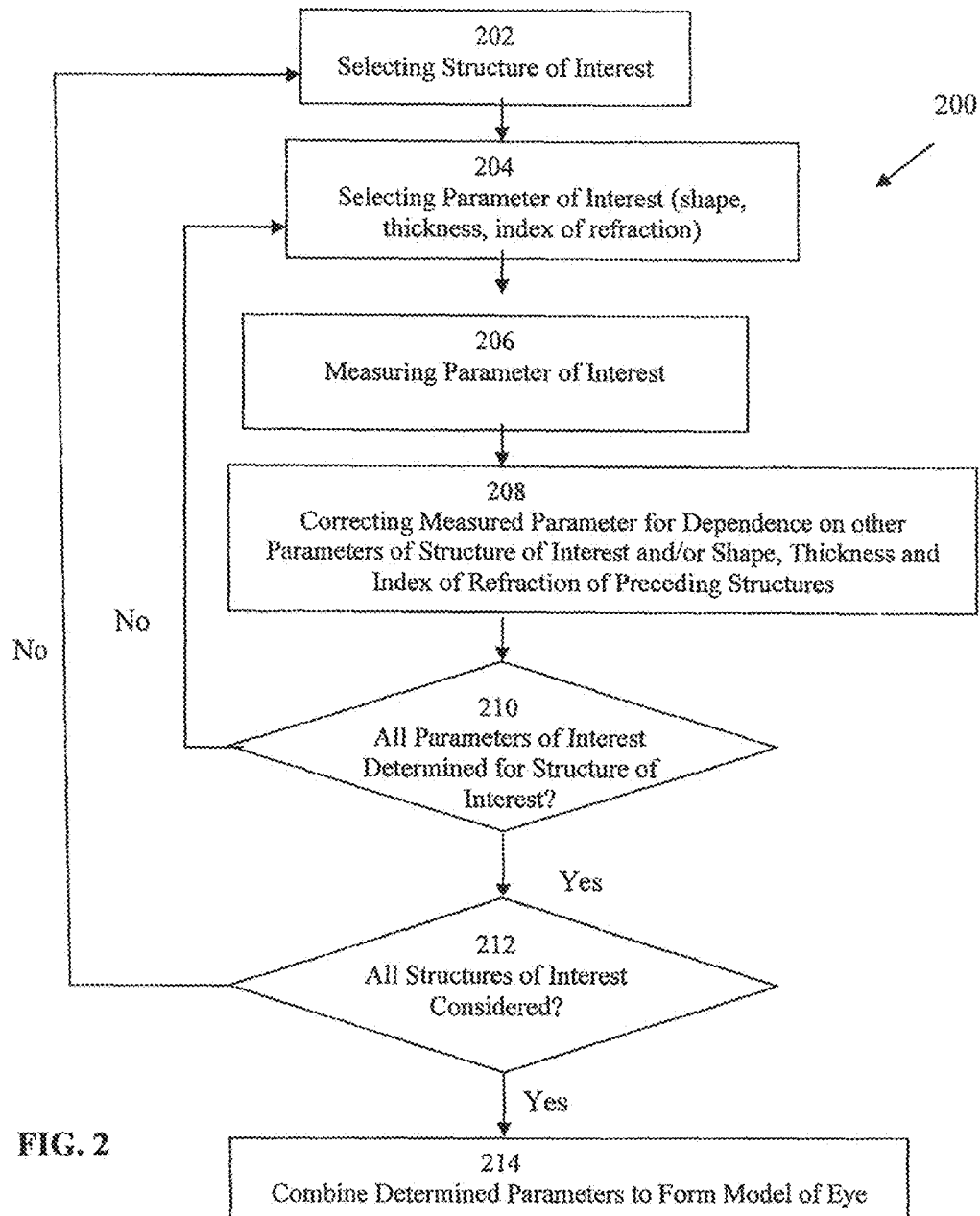
FIG. 2 illustrates a process sequence for developing a model of an ocular structure, according to one embodiment of the invention.

FIG. 2 illustrates a method of modeling ocular structures, according to one embodiment of the technology. The method 200 begins at 202 by selecting the structure of interest. The structure of interest may be a complete structure (e.g., a lens) or a surface (e.g., the front of the lens). The method continues at 204 by selecting a parameter of interest. The parameter may be the shape, thickness, or refractive index of the structure of interest. Any of these three parameters may be of interest either as an ultimate result or as a means for determining other parameters, or for both purposes. For example, the shape of the cornea may be of interest as an end result for modeling the cornea, but may also facilitate determination of the refractive index of the cornea.

Subsequently, at 206, the method 200 continues by measuring the parameter of interest. For example, if the parameter of interest is shape (e.g., the shape of the front surface of the lens), the shape may be directly measured, for example using optical techniques, such as topography techniques, or in any other suitable manner.

As described generally above, depending on the type of measurement technique used for any given parameter, the directly measured value(s) of that parameter may not account for light path changes (e.g., due to differing indices of refraction of adjacent structures) within the eye. Thus, accurate determination of a given parameter of interest may involve correction of a measured value (or values) of that parameter to account for other parameters of the structure of interest and/or parameters of ocular structures preceding the ocular structure of interest. Thus, in the non-limiting example of FIG. 2, the measured parameter from 206 is corrected at 208 for its dependence (if any) on other parameters of the selected structure of interest and/or any parameters of the preceding ocular structures.

For example, the shape of the front surface of the lens may be directly measured at 206 using topography, or any other suitable technique, which measurements may then be corrected at 208 to account for the shapes of the front and back surfaces of the cornea, the thickness T1 of the cornea, the distance d1 between the back surface of the cornea and the front surface of the lens, and the indices of refraction of the cornea (n1) and the aqueous (n2).

It should be appreciated that a measured value from 206 may depend on one or more parameters whose values are not yet known at 208 (e.g., have not yet been measured).

For example, the shape of the front surface 116a of the lens 104 may be directly measured, and, depending on the measurement technique used, the measured shape may depend on the refractive index n1 of cornea 102, which may not have been measured as of the time the method proceeds to 208. Accordingly, the method 200 may be iteratively performed to correct a measured value's dependence on all parameters on which it depends, regardless of the order in which the various parameters are determined. A similar result may be achieved using an alternative to the method 200, in which correction may be performed at 214, as described below, rather than at 208, after all parameters have been measured. However, generally speaking, the corrections may be performed at various times during the methodology, and the various aspects described herein are not limited to performing corrections of directly measured values at any particular act.

Next, at 210, a determination is made whether all the parameters of interest for the structure of interest have been determined. For example, performance of acts 204-208 may return the thickness of a particular structure (e.g., of a lens), but it may still be desired to determine the shape of the lens. Thus, if not all parameters for a given structure of interest have been determined, the method may return to 204, where the next parameter of interest for the structure of interest may be selected.

If, at 210, it is determined that all the parameters of interest have been determined for the structure of interest, the method proceeds to 212, at which a determination is made whether all the structures of interest have been examined. If not, the method may return to 202, where the next structure (e.g., complete structure or surface) may be selected.

Once all the parameters of interest have been determined for all of the structure(s) of interest, the parameters may be combined at 214 to form a model of the structures. In some embodiments, the model may indicate the shapes and locations of the structures, although not all embodiments are limited in this respect. The model produced at 214 may be used to assess the function of the structures, to predict any changes in function that will be caused by modifications of the structures (e.g., during surgery or otherwise), to predict the performance of ocular implants (e.g., lens implants, corneal implants, etc.), to plan optical surgeries, or for any other reason, as the various aspects described herein are not limited to using models of ocular structures for any particular purpose(s). Analysis of the optical performance of the modeled structures may be performed using ray tracing software, or in any other suitable manner.

As mentioned the method 200 may be iterative, with the number of iterations depending in some non-limiting embodiments on the number of structures and/or the number of parameters of interest. In addition, as mentioned previously, it should be appreciated that the correction performed at 208 may rely on parameters not yet determined as of act 208. Thus, correction of measured parameters may also, or alternatively, be performed during the combination of the parameters at 214, once all the parameters of interest have been measured.

The method 200 may be applied to any one or more structures of the eye. Thus, while the non-limiting illustration of method 200 ends with the formation of a model of the eye at 214, it should be appreciated that this is one non-limiting end result of the method. Alternatively, the method may be used to model only a single structure (e.g., a lens, or a surface of a lens), or in some situations, only to determine a single parameter of interest for which the measured value(s) may depend on other parameters. For example, determination of the refractive index of a lens may be the desired outcome, and only a subset of the acts of method 200 may be performed to achieve an accurate value of the refractive index.

The method 200 may be implemented in various manners, and the various aspects of the technology described herein applying method 200 are not limited to utilizing the method in any particular manner. For example, any suitable combination of hardware and/or software may be employed to perform one or more of the acts of method 200.

According to some embodiments, separate instruments are used to measure the various parameters of interest, i.e., separate instruments are used to measure thicknesses/distances, the indices of refraction, and the shapes of the structure(s) of interest. For example, an interferometer may be used to measure the thicknesses/distances of interest, while a topographer (e.g., a Scheimpflug topographer, or any other suitable type of topographer) may be used to measure the shape of a given structure, and a refractometer may be used to determine the indices of refraction of interest. Hardware, software, and/or manual calculations may be employed to perform the corrections and determinations of method 200 (i.e., acts 208, 210 and 212). For example, in one embodiment, the outputs of the various instruments are sent to one or more processors for performing the corrections, determinations, and the combinations of the determined parameters.

Alternatively, according to other embodiments, the measurements of parameters of interest may be performed using an apparatus configured to measure two or more of the parameters. According to one embodiment, an apparatus utilizes different instruments for measuring the thicknesses/distances of interest and for measuring the indices of refraction and the shape of ocular structures. In one non-limiting embodiment, an apparatus includes an interferometer for measuring thicknesses/distances, and a laser array with multiple imaging devices (e.g., cameras) to determine the shapes of surfaces and the indices of refraction of interest.

Regardless of the types and number of instruments used to measure the parameters of interest, the resulting parameters may be combined to form a model of the structures of interest using any combination of hardware, software, and/or manual calculations, or in any other suitable manner. For example, according to one embodiment, ray tracing software (e.g., Matlab from the MathWorks Inc., Natick, Mass.; Zemax Focus Software from Zemax, Tucson, Ariz.; Optimas from MediaCybernetics, Visual Basic, or any other suitable software) is used at 214 to combine the determined parameters. Other techniques may also be employed.

As mentioned, the method 200 may be used to model any one or more ocular structures, or to determine desired individual parameters of ocular structures. However, for purposes of illustration, two non-limiting examples of the application of method 200 to the modeling of the cornea and lens of an eye are now described. It should be appreciated that the method 200 is not limited to these two implementations, and that other implementations are possible.

Figure 3:
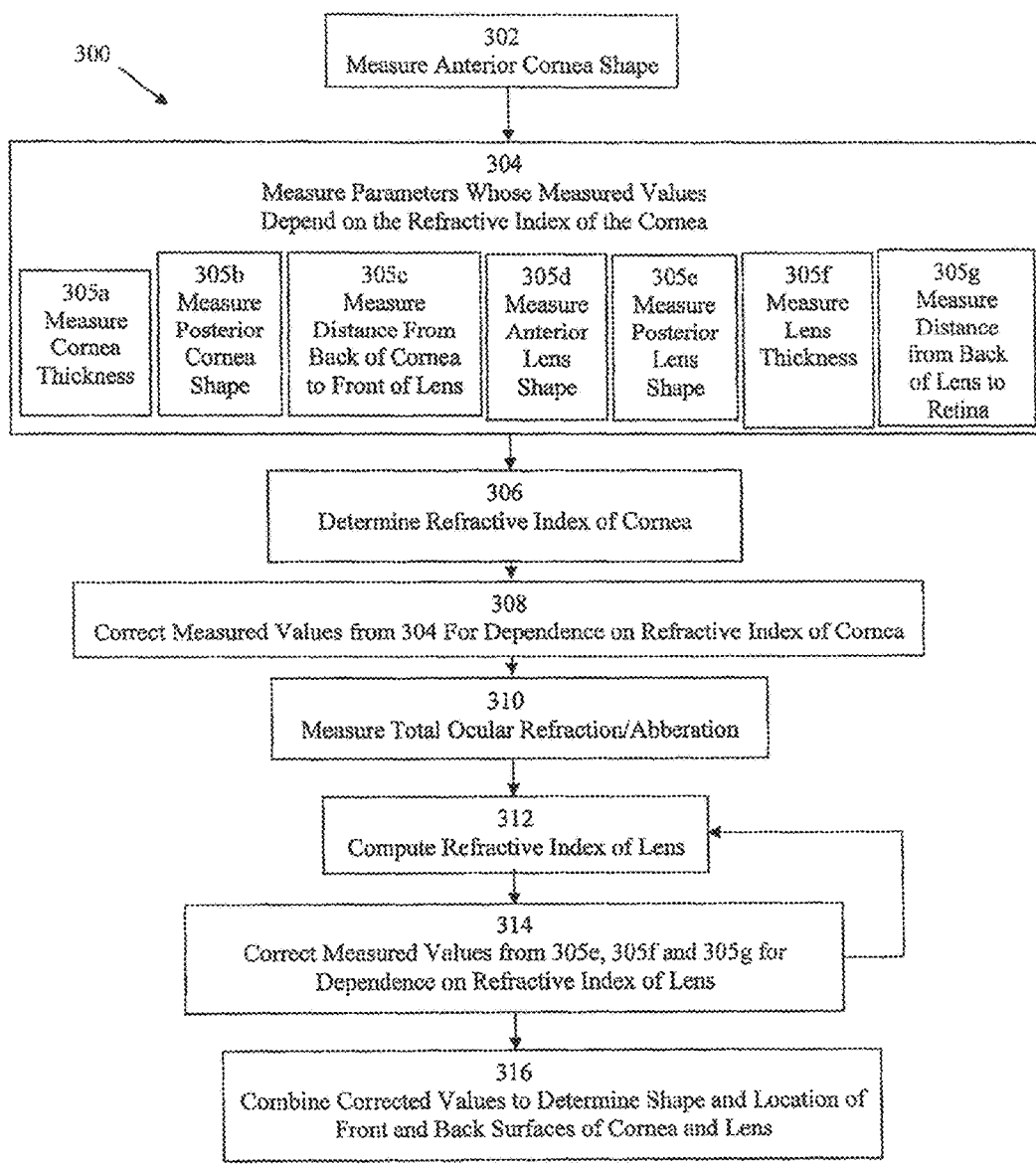
FIG. 3 illustrates one non-limiting implementation of the process of FIG. 2 to determine the shape and location of the front and back surfaces of the cornea and the front and back surfaces of the lens, according to one embodiment of the present invention.
Figure 4:
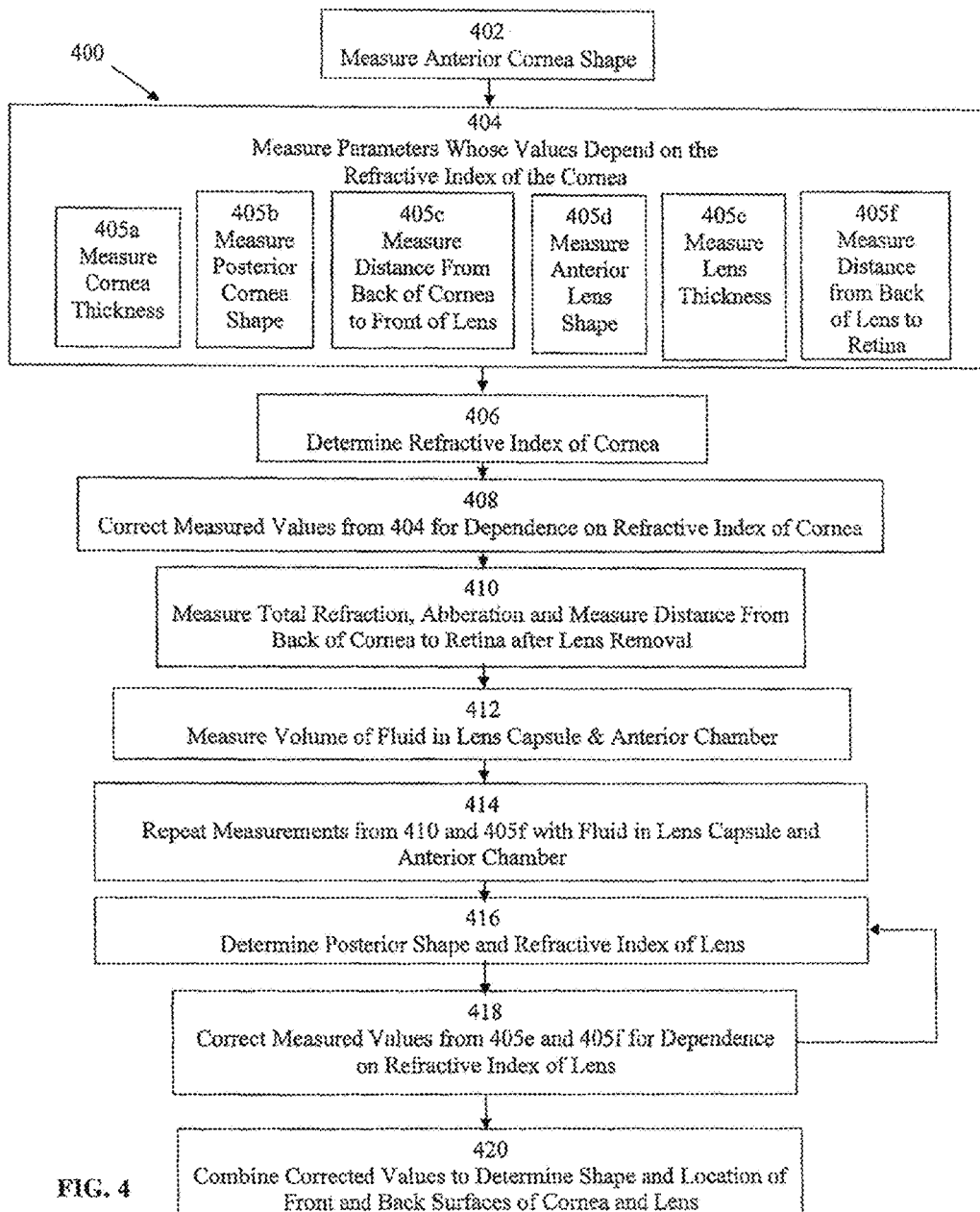
FIG. 4 illustrates an alternative non-limiting implementation of the process of FIG. 2 to determine the shape and location of the front and back surfaces of the cornea and the front and back surfaces of the lens, according to one embodiment of the invention.

The methods of FIGS. 3 and 4 illustrate alternative implementations of the method 200 to model the shapes and locations of the front and back surfaces of the cornea and lens. The differences between methods 300 and 400 may arise from the types of information known and sought, and thus may depend on the operative stage at which the methods are applied. For example, the method 300 of FIG. 3 may be applied at a pre-operative stage, while the method 400 may be applied at an intra-operative or post-operative stage. However, the methods 300 and 400 are not limited to being applied at any particular stage of an ocular procedure.

As mentioned, methods 300 and 400 relate to modeling the front and back surfaces of the cornea and the front and back surfaces of the lens. Multiple parameters may therefore be measured in performing methods 300 and 400, while others may be determined or calculated without measurement. As has been described with respect to FIG. 2, measured parameters may subsequently be corrected for any dependence the measured parameter has on other parameters. As has also been mentioned, whether a measured value of a parameter depends on other parameters may depend on the manner in which the measured value is measured, for example including the type of instrument used. For methods 300 and 400, it is assumed that measured shapes are measured using a topographer (e.g., a Scheimpflug topographer, or any other suitable topographer), and that measured thicknesses are measured using an interferometer (e.g., a multiple wavelength low or partial coherence interferometer). However, it should be appreciated that method 200 may be implemented in other manners, and that methods 300 and 400 are merely two non-limiting examples. It will be appreciated that shapes and distances may also be measured using one or more methods and is not restricted to instruments including Scheimpflug, Purkinje or time-flight principles (such as tomographers or optical coherence tomographers).

As a preliminary matter, the method 300 involves measuring several parameters of the eye, including: anterior cornea shape; cornea thickness; posterior cornea shape; distance from the back surface of the cornea to the front surface of the lens; anterior lens shape; posterior lens shape; lens thickness; distance from the back surface of the lens to the retina; and the total ocular refraction/aberration. As mentioned previously, method 300 assumes that measured shapes are measured using a topographer, and that measured distances/thicknesses are measured using an interferometer. As a result of those measurement techniques, the above-listed measured parameters may have the following dependencies. The measured cornea thickness may depend on the refractive index of the cornea. The measured posterior cornea shape may depend on the refractive index of the cornea, the anterior cornea shape, and the cornea thickness. The measured distance from back surface of the cornea to front surface of the lens may depend on the refractive index of the cornea. The measured anterior lens shape may depend on the refractive index of the cornea, the anterior cornea shape, the posterior cornea shape, the cornea thickness, and the distance from the back of the cornea to the front surface of the lens. The measured posterior lens shape may depend on the refractive index of the cornea, the anterior cornea shape, the cornea thickness, the posterior cornea shape, the distance from the back surface of the cornea to the front surface of the lens, the anterior lens shape, the posterior lens shape, the lens thickness, the distance from the back surface of the lens to the retina, the total ocular refraction/aberration, and the refractive index of the lens. The measured lens thickness may depend on the refractive index of the cornea and the refractive index of the lens. The measured distance from the back surface of the lens to the retina may depend on the refractive index of the cornea and the refractive index of the lens. Thus, the method 300 accounts for these dependencies by suitably correcting the measured values.

It should be appreciated that, given the interdependency of several of the measured parameters in method 300, the method may be implemented in any suitable order. In addition, one or more acts of the method may be implemented in parallel. However, for purposes of illustration, method 300 provides one non-limiting example of a suitable ordering of acts and sub-acts. Briefly, the method involves measure parameters whose values depend on the refractive index of the cornea. The refractive index of the cornea is then determined, and the previously measured parameters are corrected to account for their dependence on the corneal refractive index. The total ocular refraction or aberration may also be measured. Then, by suitably combining the corrected parameters and the total ocular refraction or aberration, the refractive index of the lens may be determined. With that information, the lens thickness, the shape of the posterior lens surface, and the distance from the back surface of the lens to the retina may be accurately determined. Two or more of the determined values may then be combined to model the cornea and lens. As with method 200, the methods 300 and 400 may be iterative, and are not limited to performing any particular acts of the method first. Rather, various acts may be performed in parallel, or in any one of various serial sequences. Thus, the ordering described is not limiting.

Referring to FIG. 3, the method 300 begins at 302 by measuring the anterior cornea shape, i.e., the shape of the front surface of the cornea. As previously mentioned, such measurements of shape in the method 300 are presumed to be performed using a topographer, however not all embodiments are limited in this respect.

At 304, various parameters whose measured values depend on the refractive index of the cornea may be measured. In the non-limiting example of FIG. 3, these include measuring the thickness of the cornea (at 305a), measuring the posterior cornea shape (at 305b), i.e., the shape of the back surface of the cornea, measuring the distance from the back surface of the cornea to the front surface of the lens (at 305c), measuring the anterior lens shape (at 305d), i.e., the shape of the front surface of the lens, measuring the posterior lens shape (at 305e), i.e., the shape of the back surface of the lens, measuring the thickness of the lens (at 305f), and measuring the distance from the back surface of the lens to the retina (at 305g). While each of these measured values may depend on the refractive index of the cornea in the non-limiting example of method 300, one or more may also depend on additional parameters. For example, the measured posterior lens shape, measured lens thickness, and measured distance from the back surface of the lens to the retina may also depend on the refractive index of the lens.

The refractive index of the cornea may be determined at 306. This may be done in various ways. According to one embodiment, the refractive index of the cornea is determined by direct measurement, for example using a refractometer (e.g., to determine the critical angle of total internal reflection of the cornea). For example, a refractometer operating by the principle of total internal reflection may provide a composite refractive index of the cornea at yellow wavelengths. However, not all embodiments are limited to using this type of refractometer. Such a measurement may be corrected for any dependence the measured value may have on the wavelengths of light used by the refractometer, as well as the measured cornea thickness from 305a, the measured posterior cornea shape from 305b, and the measured anterior cornea shape from 302. Alternatively, the corneal refractive index may be calculated by suitably combining the measured cornea thickness from 305a, the measured posterior cornea shape from 305b, and the measured anterior cornea shape from 302. Alternatively, the refractive index of the cornea may be determined by using any two optical methods to independently measure the corneal thickness, thus producing different measured thickness values which may depend on the refractive index of the cornea, and then accounting for the differently measured thickness values. By knowing the manner in which the two methods differ (e.g., utilizing different wavelengths, etc.), the refractive index may be determined from the differently measured thickness values. For example, according to one embodiment, the refractive index of the cornea may be determined by measuring the corneal thickness with interferometry and with Scheimpflug topography, and then accounting for the differences in the measured corneal thickness values produced by these two instruments, which may operate at different wavelengths. From the different measured thickness values at the different wavelengths, the refractive index may be calculated. Thus, act 306 is not limited to any particular method of determining the refractive index of the cornea. At 308, the measured values from 304 may be corrected for their dependence on the refractive index of the cornea determined at 306, for example using the techniques described in: Navarro R. The Optical Design of the Human Eye: a Critical Review. Journal Of Optometry. 2009; 2(1):3-18; Dubbelman M, van der Heijde G L, Weeber H A. The Thickness of the Aging Human Lens Obtained from Corrected Scheimpflug Images. Optometry and Visual Science. 2001; 78(6): 411-416; and Drexler W, Hitzenberger C K, Baumgartner A, Findl O, Sattmann H, Fercher A F. Investigation of dispersion effects in ocular media by multiple wavelength partial coherence interferometry. Exp. Eye Res. 1998; 66, 25-33, all of which are hereby incorporated herein by reference in their entireties. Other techniques are also possible.

As mentioned, some of the measured values from 304 may also depend on the refractive index of the lens. According to the non-limiting example of method 300, the refractive index of the lens is calculated, rather than measured. To facilitate this computation, the total ocular refraction/aberration may be measured at 310. This measurement may be made using a refractometer (e.g., an ocular autorefractometer, a Hartmann Schack abberometer, Talbot-Morie interferometer, or any other suitable instrument), or any other suitable technique.

Subsequently, at 312, the refractive index of the lens may be computed by suitably combining the values from 302-310. Non-limiting examples of techniques which may be used in this step include those described in: Dubbelman M, van der Heijde G L, Weeber H A. The Thickness of the Aging Human Lens Obtained from Corrected Scheimpflug Images. Optometry and Visual Science. 2001; 78(6): 411-416; and Rosales P, Marcos S. Pentacam Scheimpflug quantitative imaging of the crystalline lens and intraocular lens. J Refract Surg. 2009 May; 25(5):421-8, which are hereby incorporated herein by reference in their entireties. Other techniques may also be used. According to some embodiments, the computed refractive index of the lens is a composite value of the refractive index of the lens, and may be computed by matching the composite refractive index of the lens, corrected posterior lens topography, and lens thickness to the total composite refraction or total composite aberrometry of the eye from 310.

Once the refractive index of the lens is known, those previously measured values which have some dependence on the refractive index of the lens may be corrected. For example, at 314, the measured values from 305e, 305f, and 305g may be corrected for their dependence on the refractive index of the lens, for example using the techniques described in Rosales P, Marcos S. Pentacam Scheimpflug quantitative imaging of the crystalline lens and intraocular lens. J Refract Surg. 2009 May; 25(5):421-8, which is hereby incorporated herein by reference in its entirety, or any other suitable techniques.

It should be appreciated that acts 312 and 314 are interrelated, in that the computation of the refractive index of the lens depends on the values measured at 305e, 305f, and 305g, and yet the measured values from 305e, 305f, and 305g depend on the refractive index of the lens. Therefore, iteration between acts 312 and 314 may be performed to provide a desired level of accuracy. Method 300 is not limited to using any particular number of iterations of acts 312 and 314.

Once all of the measured values have been corrected for their dependencies on any other parameters of interest, the method may proceed to 316, at which the corrected values may be suitably combined to determine the shapes and locations of the front and back surfaces of the cornea and lens. Ray tracing software, or any suitable combination of hardware, software, and manual calculations may be used to perform the combinations to determined the shapes and locations of the front and back surfaces of the cornea and lens.

The various computations and combinations in method 300 may be performed using any suitable combination of hardware, software, and/or manual calculations. For example, ray tracing software may be used to perform one or more of the acts in method 300. Other implementations are also possible.

FIG. 4 illustrates an alternative non-limiting example of the application of method 200 to the determination of the front and back surfaces of the cornea and the front and back surfaces of the lens. The method 400 is applied in an intra-operative or post-operative setting, and thus at a different stage than the method 300, which illustrated a pre-operative setting. For example, the method 400 may be applied when a patient's lens is to be replaced, therefore involving removal of the lens.

As with the method 300, method 400 presumes that measured shapes are measured using a topographer, and that measured distances/thicknesses are measured using an interferometer. It will be appreciated that shapes and distances may also be measured using one or more methods and is not restricted to instruments including Scheimpflug, Purkinje or time-flight principles (such as tomographers or optical coherence tomographers). Thus, as with method 300, many of the values measured in method 400 may depend on other parameters. For example, method 400 involves measuring the following: anterior cornea shape; cornea thickness; posterior cornea shape; distance from the back surface of the cornea to the front surface of the lens; anterior lens shape; lens thickness; distance from the back surface of the lens to the retina; total ocular refraction and aberration in the absence of the lens; distance from the back surface of the cornea to the retina in the absence of the lens; total volume of fluid in the lens capsule and anterior chamber (described below); total refraction and aberration with fluid in the lens capsule and anterior chamber; and the distance from the back of the cornea to the retina with fluid in the lens capsule and the anterior chamber. Alternatively several of the instruments mentioned above may be used to measure the posterior curvature of the lens in the absence of the lens.

As has been mentioned, the measurement of various parameters may produce results which depend on one or more other parameters, for example as a result of the measurement technique employed. Thus, one or more of the above-mentioned measured values in method 400 may depend on one or more other parameters. For example, the measured cornea thickness may depend on the refractive index of the cornea. The measured posterior cornea shape may depend on the refractive index of the cornea, the anterior cornea shape, and the cornea thickness. The measured distance from the back surface of the cornea to the front surface of the lens may depend on the refractive index of the cornea. The measured anterior lens shape may depend on the refractive index of the cornea, the anterior cornea shape, the cornea thickness, the posterior cornea shape, and the distance from the back surface of the cornea to the front surface of the lens. The measured lens thickness may depend on the refractive index of the cornea and the refractive index of the lens. A measured value of the refractive index of the cornea may depend on the wavelength used to measure the cornea thickness, the anterior cornea shape, the cornea thickness, and the posterior cornea shape. A measured value of the distance from the back surface of the cornea to the retina after removal of the lens may depend on the refractive index of the cornea.

Measured values of the total ocular refraction and aberration, and the distance from the back surface of the cornea to the retina, as well as the distance from the back of the lens to the retina with fluid in the lens capsule and anterior chamber (described below) may depend on the refractive index of the cornea, the measured volume of fluid in the lens capsule and anterior chamber, and the refractive index of this fluid. Measured values of the posterior lens shape may depend on the anterior cornea shape, the cornea thickness, the posterior cornea shape, the distance from the back surface of the cornea to the front surface of the lens, the anterior lens shape, the lens thickness, the distance from the back surface of the lens to the retina, the refractive index of the cornea, the total ocular refraction and aberration after lens removal, the distance from the back surface of the cornea to the retina after lens removal, the volume of fluid inserted in the lens capsule and anterior chamber, the distance from the back surface of the lens to the retina with fluid in the anterior chamber, the total ocular refraction and aberration with fluid in the lens capsule and anterior chamber, the distance from the back surface of the cornea to the retina with fluid in the lens capsule and anterior chamber, the refractive index of the lens, and the refractive index of the fluid. Thus, method 400 may account for such dependencies.

The method 400 begins at 402 with the measurement of the anterior cornea shape, i.e., the shape of the front surface of the cornea. At 404, measurements are made of those parameters whose values depend on the refractive index of the cornea in this non-limiting example. Those values include measuring the thickness of the cornea (at 405*a*), measuring the posterior cornea shape (at 405*b*), measuring the distance from the back surface of the cornea to the front surface of the lens (at 405*c*), measuring the anterior lens shape (at 405*d*), measuring the thickness of the lens (at 405*e*), and measuring the distance from the back surface of the lens to the retina (at 405*f*).

At 406, the refractive index of the cornea may be determined. This may be determined in any suitable manner, including using any of the techniques described previously for act 306 of method 300, or in any other suitable manner. With the refractive index of the cornea determined, method 400 may continue at 408 by correcting the measured values from 404 for their dependence on the refractive index of the cornea, for example using techniques described in the previously cited reference to Rosales (Scheimpflug quantitative imaging of the crystalline lens and intraocular lens), or any other suitable techniques.

As mentioned, the method 400 may apply to a situation in which a patient's natural lens is to be removed (e.g., for replacement by an implant). Thus, at 410, several additional measurements are made, presuming that the lens has been removed. These measurements include measuring the total refraction, the total aberration, and the distance from the back surface of the cornea to the retina in the absence of the lens. Alternatively several of the instruments mentioned above may be used to measure the posterior curvature of the lens in the absence of the lens. These measurements may be made using any suitable techniques, as the method 400 is not limited in this respect.

As part of the lens replacement procedure, fluid may be inserted into the lens capsule and/or the anterior chamber, after the patient's natural lens has been removed. Measurements may be made with this fluid in place, and may provide additional data which may be utilized in the modeling procedure. In some embodiments, the fluid may have a known refractive index, although not all embodiments are limited in this respect. At 412, the volume of the fluid inserted in the lens capsule may be measured, as well as the volume of the fluid inserted in the anterior chamber. These volumes may be measured by using a graduated syringe, or in any other suitable manner, as the method 400 is not limited in this respect.

Next, at 414, the measurements of 410 and 405*f* may be repeated in this non-limiting example with the fluid in the lens capsule and anterior chamber. Thus, the measurements at 414 may provide different results than those initially made at 410 and 405*f* if the fluid inserted into the lens capsule and/or anterior chamber has a different refractive index than the refractive index of the patient's natural lens and/or the aqueous, for example. These differing values may provide additional data points which may be used in modeling.

At 416, the posterior lens shape and the refractive index of the lens may be determined. These may determined in any suitable manner, such as by suitably combining two or more of the previously determined values. For example, the posterior lens shape may be determined by suitably combining the anterior cornea shape, the values measured at 404, the refractive index of the cornea, the values measured at 410, the volumes determined at 412, the values measured at 414, the refractive index of the lens, and the refractive index of the fluid. Similarly, the refractive index of the lens may depend on the values determined prior to act 416, and therefore may be determined by suitably combining these values, for example using techniques described in the previously cited references to Dubbelman (The Thickness of the Aging Human Lens Obtained from Corrected Scheimpflug Images) and Rosales (Scheimpflug quantitative imaging of the crystalline lens and intraocular lens), or any other suitable techniques. In some embodiments, the volumes of fluid inserted into the lens capsule and anterior chamber after removal of the patient's lens may be approximately equal to the volumes of the patient's lens and the aqueous, respectively. The determinations at 416 may take any such relationship into account as appropriate.

At 418, method 400 continues by correcting the measured values from 405*e* and 405*f* for their dependence on the refractive index of the lens determined at 416. This may be done using the techniques described in the previously cited references to Dubbelman (The Thickness of the Aging Human Lens Obtained from Corrected Scheimpflug Images) and Drexler (Investigation of dispersion effects in ocular media by multiple wavelength partial coherence interferometry), or any other suitable techniques. Thus, it should be appreciated that acts 416 and 418 may depend on each other, in that the determination of the refractive index of the lens at 416 may depend on the lens thickness, and the distance from the back surface of the lens to the retina, while the measured values of the lens thickness and the distance from the back surface of the lens to the retina may in turn depend on the refractive index of the lens. Thus, acts 416 and 418 may be iterated any number of times to provide a desired degree of accuracy of the values determined by those acts. Subsequently, at 420, any two or more of the parameter values determined during method 400 may be combined to determine the shape and location of the front and back surfaces of the cornea and the lens. As with method 300, it should be appreciated that method 400 is one non-limiting example of an order in which the acts illustrated may be performed. However, other orders are also possible and one or more of the acts may be performed in parallel, as the method is not limited in this respect.

Figure 5:
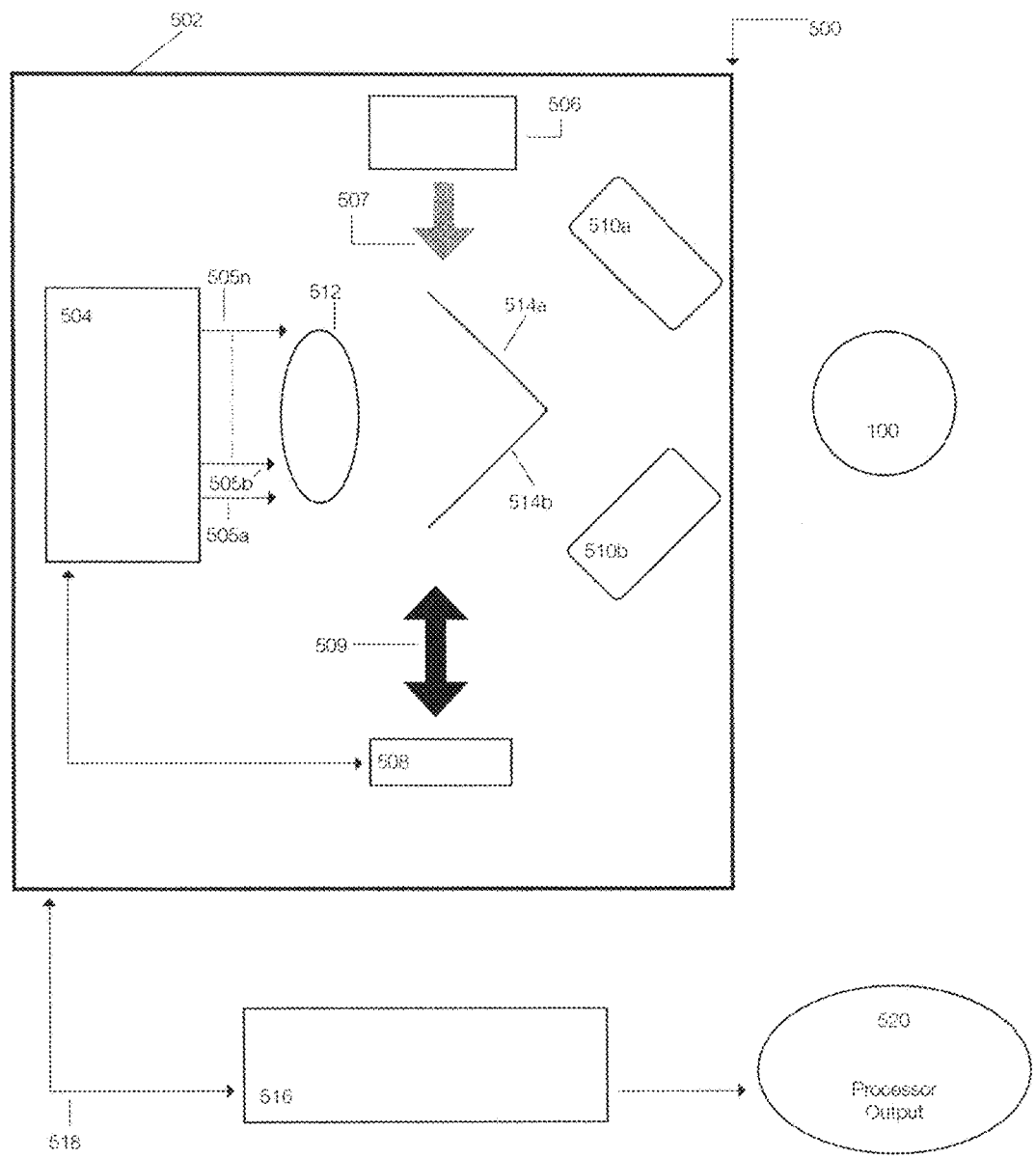
FIG. 5 illustrates an apparatus comprising a laser array source for measuring indices of refraction and shapes of ocular surfaces, according to one non-limiting embodiment of the invention.

While methods 300 and 400 illustrate non-limiting implementations of the method 200 utilizing different instruments to measure distances, shapes, and indices of refraction, not all implementations of method 200 are limited in this respect. For example, as previously mentioned, according to some embodiments, the method 200 may be implemented using an apparatus that integrates the functionality of an interferometer, a topographer, and a refractometer, or any other functions. According to one aspect of the technology described herein, an apparatus comprises a laser array source which may be used to measure surface shapes and indices of refraction. One non-limiting example of such an apparatus is illustrated in FIG. 5, together with the eye 100 of FIG. 1.

As shown, the apparatus 500 comprises a ray tracing apparatus 502. The ray tracing apparatus 502 comprises a laser array source 504, which produces an array of laser beams 505a, 505b, . . . , 505n. In addition, the ray tracing apparatus 502 comprises a reference beam generator 506 for producing a reference point beam 507 (alternatively referred to herein as a "fixation laser"), and an interferometer source 508 for producing an interferometry signal 509. Multiple imaging devices 510a and 510b may also be included in the ray tracing apparatus 502. In addition, various optical components may be included for directing/controlling the various optical signals generated by the apparatus 502, such as an element 512 (which may in some situations be a lens and/or a mirror, as described below) and beam splitters 514a and 514b. It should be appreciated that other optical components may also be included, as the apparatus described herein are not limited to using any particular optical components for directly/controlling optical signals. The apparatus 500 may further comprise one or more processors 516 coupled to the apparatus 502 to receive and process signals from the apparatus 502. According to some embodiments, the processor 516 may utilize ray tracing software, or any other suitable processing techniques, as described further below. Although not shown, iris recognition technology may optionally be included in the apparatus 502, for example to facilitate repeatability of measurements through the visual axis.

The laser array source 504 may generate the array of laser beams 505a . . . 505n, which beams may be projected onto the eye 100. As described in further detail below, the array may be controlled to be focused on a particular surface of the eye if desired, although not all embodiments are limited in this respect. The array of laser beams 505a . . . 505n may generate a pattern of laser spots on each surface it contacts. The spacing between the spots of the pattern may be used to determine the shape of the surface on which the pattern appears. Also, the spacing between the spots may be used to determine the refractive index of an ocular material through which the laser beams 505a . . . 505n have passed.

The laser array source 504 may comprise any number of laser beams 505a . . . 505n. An array with a larger number of beams may provide greater accuracy in determinations of surface shapes and indices of refraction based on a pattern of laser spots corresponding to the array. However, the various aspects described herein implementing an apparatus with a laser array source are not limited to using any number of laser beams. According to some embodiments, the laser array source 504 generates at least twelve laser beams. According to one embodiment, the laser array source generates sixteen laser beams. According to some embodiments, the laser array source may generate between 16-256 laser beams.

Again, the laser array source 504 is not limited to generating any particular number of laser beams.

The laser beams may have any suitable sizes (e.g., diameters) and cross-section shapes. According to one embodiment, the diameters of the laser beams are as small as possible (e.g., as small as may be detectable with the imaging devices 510a and 510b), which may facilitate inclusion of a larger number of beams in the array. However, the laser beams are not limited to having any particular diameters. According to some embodiments, the laser array may have a tight point spread function. The laser beams may have a circular cross-section, an oval cross-section, a star-shaped cross-section, a hexagonal cross-section, or any other suitable cross-section. Thus, it should be appreciated that the lasers described herein are not limited to having any particular cross-section shapes.

The laser beams 505a . . . 505n may have any suitable wavelengths. As will be described further below, some values of ocular parameters measured using a laser array may depend on the wavelengths of the lasers of the array, such that the measured values may be corrected to account for their dependence on the wavelengths. In addition, by utilizing multiple wavelengths (e.g., a laser source having variable wavelength lasers), additional data points at the various laser wavelengths may be collected, which may increase the accuracy of calculations of refractive index and shape using the laser array. For example, utilizing multiple wavelengths may enable production of a graph of refractive index as a function of wavelength. According to some embodiment, the laser array may include lasers having infrared wavelengths, which may be used to determine approximate values of surface temperatures of the ocular surfaces on which the laser impinge. According to some embodiments, the array of laser beams may comprise laser beams of two or more different wavelengths (e.g., red and green wavelengths). However, the laser beams 505a . . . 505n are not limited to having any particular wavelengths. According to some embodiments, the lasers have short pulses to facilitate an increase in resolution of the laser array.

According to some embodiments, the array of laser beams may be scanned over the eye 100. In such embodiments, any suitable scan time may be used. Using a shorter duration scan time may reduce the impact of ocular movement on the measurements utilizing the laser array.

According to one embodiment, the laser array source may be adjustable, for example allowing it to assume various angles with respect to the eye 100. By projecting the laser beams onto the eye from various angles, additional data points may be collected compared to if the laser array source is fixed at a single location. According to some embodiments, the laser array source and imaging devices may be positioned and angled according to Scheimpflug principles, although not all embodiments are limited in this respect.

As mentioned, the array of laser beams 505a . . . 505n may be directed onto one or more surfaces of the eye 100, such as the front surface of the cornea, the back surface of the cornea, the front surface of the lens, the back surface of the lens, the retina, or any other surfaces, resulting in a pattern of laser spots on those surfaces. The element 512 and the beams splitters 514a and 514b may be used to control which surfaces of the eye the laser beams 505a . . . 505n impact, and whether the beams are focused on those surfaces or not. For example, the element 512 may comprise a lens (e.g., an aspheric lens) for collimating and/or converging the array of laser beams 505a . . . 505n, for example to focus the array of laser beams to a single spot on one of the ocular surfaces, as described further below. By focusing the array on different surfaces of the eye, different data points may be collected for determining indices of refraction and shapes, as described below. The use of such additional data points may increase the accuracy of the determined values of the refractive index and shape. While element 512 may comprise one or more lenses, it may alternatively, or in addition, comprise a mirror, which is some cases may be a deformable mirror, to direct the laser beams 505a . . . 505n.

The imaging devices 510a and 510b may be configured and used to capture images of the pattern(s) of laser spots on one or more of the ocular surfaces of eye 100 resulting from the array of laser beams 505a . . . 505n. According to one embodiment, the imaging devices 510a and 510b may be positioned approximately symmetrically on opposite sides of the laser array (e.g., on right and left sides, top and bottom, etc). In some embodiments, positioning the imaging devices symmetrically about the laser array may result in the imaging devices being symmetrically positioned about the laser array source. In addition, the imaging devices 510a and 510b may be substantially equidistant from the eye 100.

According to some embodiments, the imaging devices 510a and 510b may be positioned according to Scheimpflug principles. While the imaging devices 510a and 510b capture slightly different images of any pattern of laser spots on the surfaces of the eye, as a result of imaging the pattern from different angles, the images captured by the two imaging devices may be combined to determine shapes of ocular surfaces and/or indices of refraction of ocular materials.

According to one embodiment, averaging the images of a same pattern of laser spots captured by imaging devices 510a and 510b may produce an averaged image from which the shape of the surface on which the pattern appears may be determined. Such an averaged image may correspond substantially to the image that would be captured by a single imager positioned at the point of the laser array source 504, if it were possible to position an imaging device there without having the laser array source impede the field of view of the imaging device. The shape of the surface may be determined from the averaged image by suitably processing the distances between the laser spots of the averaged image and comparing the distances in the averaged image to the separation distances of the laser beams at the laser array source 504. According to some embodiments, the distances between nearest neighbor spots are used. According to an alternative embodiment, the distance between a single spot and every other spot of the array is used. Other techniques are also possible. According to one embodiment, ray tracing software (e.g., any of the types previously mentioned or any other suitable ray tracing software) may perform such processing. According to another non-limiting embodiment, the techniques described in Preussner P, Wahl J, Kramann C. Corneal model. J Cataract Refract Surg 2003; 29:471-477, may be used and is incorporated herein by reference in its entirety.

According to one embodiment, taking a difference between the images of a same pattern of laser spots captured by imaging devices 510a and 510b may produce a differenced image from which the refractive index of a material may be determined. For example, the differenced image may be produced by subtracting the image captured by imaging device 510a from the image captured by imaging device 510b, or vice versa. According to one embodiment, the array of laser beams may be focused approximately to a point at a first location (e.g., on a first ocular surface), while the array forms a pattern of laser spots at a second location (e.g., on a second ocular surface). The refractive index of the material separating the first and second locations may be determined by knowing the distance between the first and second locations and then processing the distances between laser spots of the pattern of laser spots in a differenced image of the pattern at the second location. An example is described in further detail below.

The imaging devices 510a and 510b may be any suitable type of imaging devices. According to one embodiment, the imaging devices 510a and 510b are CCD imagers. However, they may alternatively be CMOS imagers, or any other suitable types of imaging devices. According to some embodiments, the imaging devices 510a and 510b are fixed, such that they do not move during operation of the apparatus 500. In this manner, the apparatus 500 may be simplified compared with systems that utilize rotating, or otherwise moving, cameras. According to some embodiments, the imaging devices may be light field cameras. Also, the imaging devices may produce still frames or video images, as the various aspects described herein are not limited in this respect.

Also, the imaging devices 510a and 510b may have any suitable resolution. A higher resolution may provide greater accuracy in determining locations of laser spots on the surfaces of the eye, and therefore may be desirable in some embodiments. In addition, an imaging device with sufficiently high resolution may enable use of a magnified image of a single reflected laser beam to serve as a proxy for the point spread function or small particle light scattering value for that reflected beam.

It should be appreciated that any number of imaging devices may be used in various embodiments. For example, while FIG. 5 illustrates two imaging devices, some embodiments may employ only a single imaging device which may rotate. According to other embodiments, between four and sixteen imaging devices may be used. Other numbers are also possible. Using a larger number of imaging devices may enhance the speed at which data may be collected. The imaging devices may be positioned at any suitable distances and/or angles relative to each other and to an eye. According to one embodiment, an array of imaging devices (e.g., including imaging devices 510a and 510b, as well as additional imaging devices) may be positioned at more than one location or angle relative to the eye, which may allow calculation of centration and triangulation of vectors of rays reflected by the eye. According to one embodiment, six imaging devices may be arranged in a substantially circular configuration. According to one embodiment, the apparatus 500 may comprise an array of imaging devices, including imaging devices 510a and 510b, which array may be used to obtain aberrometry measurements.

The source 506 may be a refractometer, an aberrometer, or any other suitable source for generating a suitable reference beam. The reference beam may provide a reference point for the imaging devices 510a and 510b, and may also, or alternatively, provide a patient a reference to look at when interacting with the apparatus.

As mentioned, the ray tracing apparatus 502 further comprises an interferometer source 508, which may be used to measure distances/thicknesses of the eye 100. According to one embodiment, the interferometer source 508 is a single wavelength low or partial coherence interferometer, such that the interferometry signal 509 may be a single wavelength low or partial coherence interferometry signal. However, not all embodiments are limited in this respect, as, for example, the interferometer source 508 may be a multiple wavelength low or partial coherence interferometer. The interferometer source 508 may be positioned so that the interferometry signal 509 is split by beam splitter 514b, with part of the split beam passing to the eye 100. Other configurations for the interferometer source 508 are also possible.

According to some embodiments the laser array source and/or interferometer source may be configured so that measurements with their optical signals are centered on the visual axis of the eye 100. According to alternative embodiments, the laser array source and/or interferometer source may be configured so that measurements with their optical signals are centered on the geometrical axis of the eye 100. Thus, it should be appreciated that various configurations are possible.

The processor 516 may be coupled to the ray tracing apparatus 502 via a connection 518 to receive outputs from the ray tracing apparatus 502. The outputs may be outputs of the imaging devices 510a and 510b and/or of the interferometer source 508. The processor may perform any suitable type of processing, such as producing the averaged images described above from imaging devices 510a and 510b, the differenced images from imaging devices 510a and 510b, performing calculations of distances between laser spots of a captured image, performing calculations to determine indices of refraction, performing calculations to determine shapes of surfaces, performing calculations to determine distances/thicknesses, or any other suitable types of processing. Accordingly, the processor 516 may be any suitable type of processor. According to some embodiments, more than one processor may be used. According to some embodiments, the processor may be integrated with the ray tracing apparatus 502, while in other embodiments it may be a distinct device.

According to some embodiments, the processor 516 may also control the ray tracing apparatus 502. For example, the processor may control the operation of one or more of the reference beam source, the laser array source, and the interferometer source. The processor 516 may send commands or instructions to one or more of those components instructing them how to behave. However, not all embodiments are limited to having the processor exhibit control functionality of the ray tracing apparatus 502.

According to some embodiments, the processor 516 may operate ray tracing software. According to some embodiments, the processor 516 may perform any of the processing acts previously described with respect to method 200, and in some embodiments may combine parameters of an eye to form a model of one or more structures of the eye as an output 520. The apparatus 500 and/or ray tracing apparatus 502 may be a stand alone desktop type device in some non-limiting embodiments. According to other embodiments, one or both may be a handheld device. According to still other embodiments, one or both may be incorporated into an operating microscope. Other configurations are also possible.

Some non-limiting examples of the operation of the array of laser beams 505a . . . 505n are now described with respect to FIGS. 6A-6E and 7A-7E. It should be appreciated that these are merely non-limiting examples.

Figure 6A:
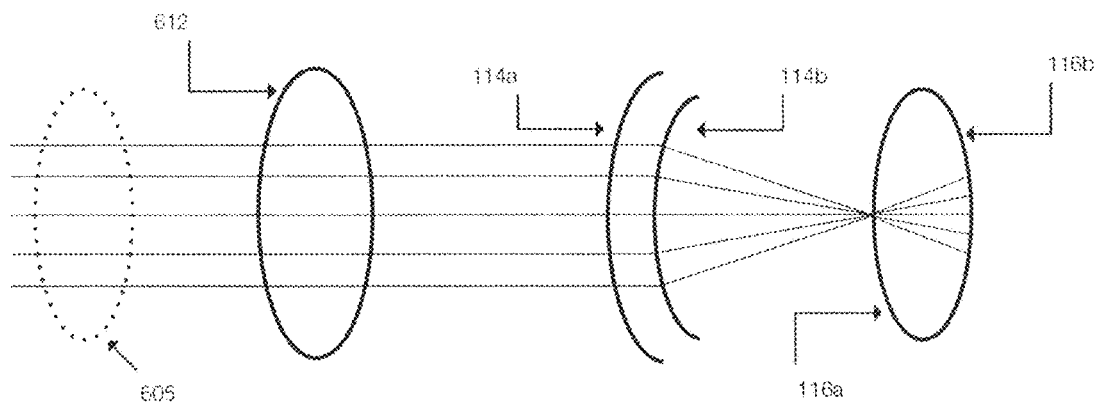
FIGS. 6A-6E illustrate configuration of a laser array source and resulting patterns of laser spots on ocular surfaces, according to one non-limiting embodiment of the invention.

FIG. 6A illustrates a non-limiting example of a configuration of a laser array with respect to the front and back surfaces of the cornea and lens of the eye 100. As shown, the laser array 605 comprises a plurality of laser beams, in this non-limiting example thirteen (although not all are visible from the perspective of FIG. 6A), which pass through a condensing lens 612 to the front surface 114a of the cornea. The laser beams then proceed to the back surface of the cornea 114b, and are focused approximately to a point on the front surface 116a of the lens. The laser beams continue to the back surface 116b of the lens. FIGS. 6B-6E show the resulting patterns of laser spots (also referred to herein as "Purkinjie images") on the front and back surfaces of the cornea and lens.

Figure 6B:
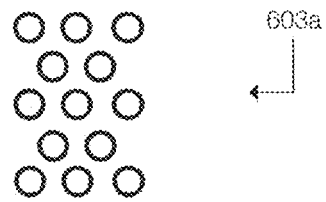

FIG. 6B shows the pattern 603a of laser spots on the front surface 114a of the cornea according to the configuration of FIG. 6A. As shown, the pattern 603a includes thirteen laser spots in this non-limiting example, corresponding to the thirteen laser beams of array 605. The pattern 603a may correspond to either an averaged image of imaging devices 510a and 510b or a differenced image of those imaging devices. The significance of the spacing between spots of the pattern 603a may depend on whether the pattern is represented in an averaged image or a differenced image.

Figure 6C:
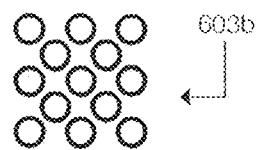

FIG. 6C illustrates the pattern 603b of laser spots appearing on the back surface 114b of the cornea. As shown in the non-limiting example of FIGS. 6A-6C, the spots of pattern 603b are more closely spaced than those of pattern 603a. However, not all embodiments are limited in this respect. As with FIG. 6B, the pattern 603b of FIG. 6C may represent either an averaged image or a differenced image of imaging devices.

Figure 6D:

FIG. 6D illustrates the pattern 603c of laser spots appearing on the front surface 116a of the lens. As shown in FIG. 6A, the array 605 of laser beams is focused approximately to a point on the front surface 116a of the lens, such that the pattern 603c includes a single point. Focusing the array 605 approximately to a point on one of the surfaces of interest may facilitate determination of an refractive index of one of the ocular materials. For example, by knowing where the array is focused to a point (i.e., the front surface 116a of the lens in the non-limiting example of FIG. 6A) and by knowing the distance from that location to a second location at which a pattern of spots appears, the distances between the spots of the pattern at the second location may be used to determine the refractive index of the material separating the two locations. As a non-limiting example, because the array 605 is focused approximately to a point on the front surface of the lens, the distances between the spots on the pattern 603b on the back surface of the cornea may be used to determine the refractive index of the aqueous between the cornea and the lens by using the distance between the back surface of the cornea (where the pattern 603b appears) and the front surface of the lens (where the array 605 is focused approximately to a point). It should be appreciated that the concept of focusing the array to a point at a known location is not limited to focusing the array to a point on a surface of the eye. Rather, according to some embodiments, the array may be focused to a point outside the eye, with the distance from the point of focus to a surface of interest on which a pattern of laser spots appears being known. Also, the focusing of an array of laser beams may be step-wise or smooth, as the various aspects described herein are not limited in this respect.

Figure 6E:
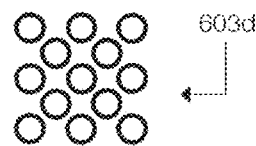

FIG. 6E illustrates the pattern 603d of laser spots appearing on the back surface 116b of the lens, corresponding to the configuration of FIG. 6A. The pattern 603d may represent an averaged image or a differenced image of imaging devices.

Figure 7A:
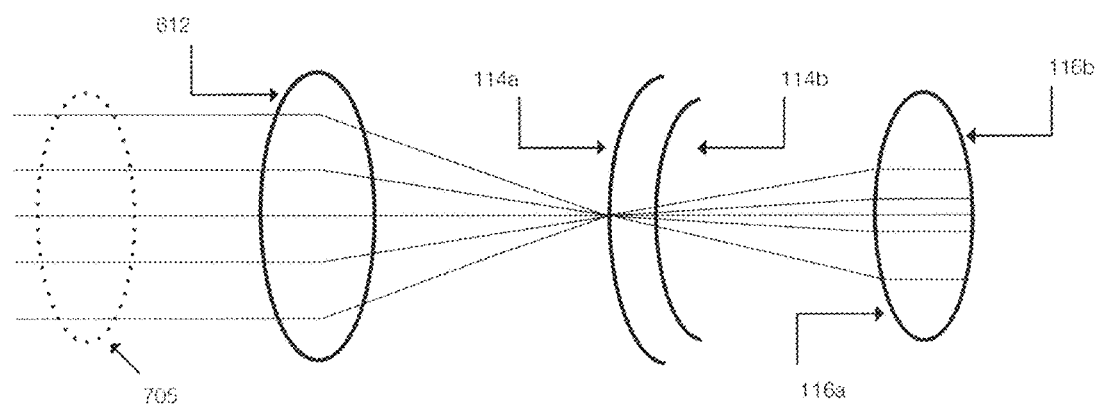
FIGS. 7A-7E illustrate an alternative configuration of a laser array source compared to that of FIG. 6A, and the resulting patterns of laser spots on ocular surfaces, according to another non-limiting embodiment of the invention.

FIGS. 7A-7E show a different configuration than that of FIGS. 6A-6E, in which an array of laser beams is focused on the front surface of the cornea rather than on the front surface of the lens. As shown in FIG. 7A, an array 705 of laser beams, including thirteen laser beams in this non-limiting example, passes through the condensing lens 612 and is focused approximately to a point on the front surface 114a of the cornea. Resulting patterns of laser spots are created as the laser beams contact the back surface of the cornea, the front surface of the lens, and the back surface of the lens.

Figure 7B:
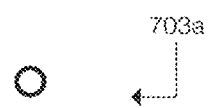
Figure 7C:
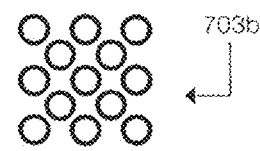
Figure 7D:
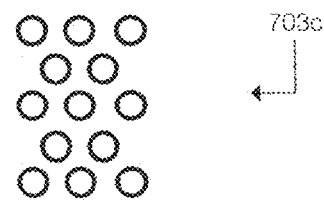
Figure 7E:
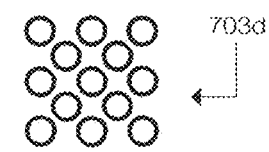

FIG. 7B illustrates the pattern 703a of laser spots appearing on the front surface 114a of the cornea for the configuration of FIG. 7A. FIG. 7C illustrates the pattern 703b appearing on the back surface 114b of the cornea for the configuration of FIG. 7A. FIG. 7D illustrates the pattern 703c of laser spots appearing on the front surface 116a of the lens for the configuration of FIG. 7A. FIG. 7E illustrates the pattern 703d of laser spots appearing on the back surface 116b of the lens for the configuration of FIG. 7A. Any of the patterns 703a-703d may represent averaged or differenced images of imaging devices such as imaging devices 510a and 510b.

While the apparatus 500 provides one non-limiting example of a suitable apparatus incorporating a laser array source and an interferometer, other apparatus may be used.

According to one embodiment, a Scheimpflug topographer is modified by replacing the slit beam source of the topographer with a laser array. The techniques described herein for using laser arrays may then be used. According to one embodiment, a Scheimpflug topographer may be modified by replacing the slit beam source with a laser array source, and by using multiple fixed cameras. For example, according to one embodiment, six fixed cameras may be used. Other configurations are also possible.

According to one embodiment, an apparatus utilizing principles of light field processing may be used. For example, an apparatus may include a laser source array and one or more light field cameras suitably arranged to image patterns of spots projected on the eye by the laser source array. Other configurations are also possible.

In addition, it should be appreciated that apparatus such as apparatus 500 are not limited to using arrays of lasers. Rather, arrays of any suitable emission may be used, and lasers represent only one suitable non-limiting example.

Figure 8:
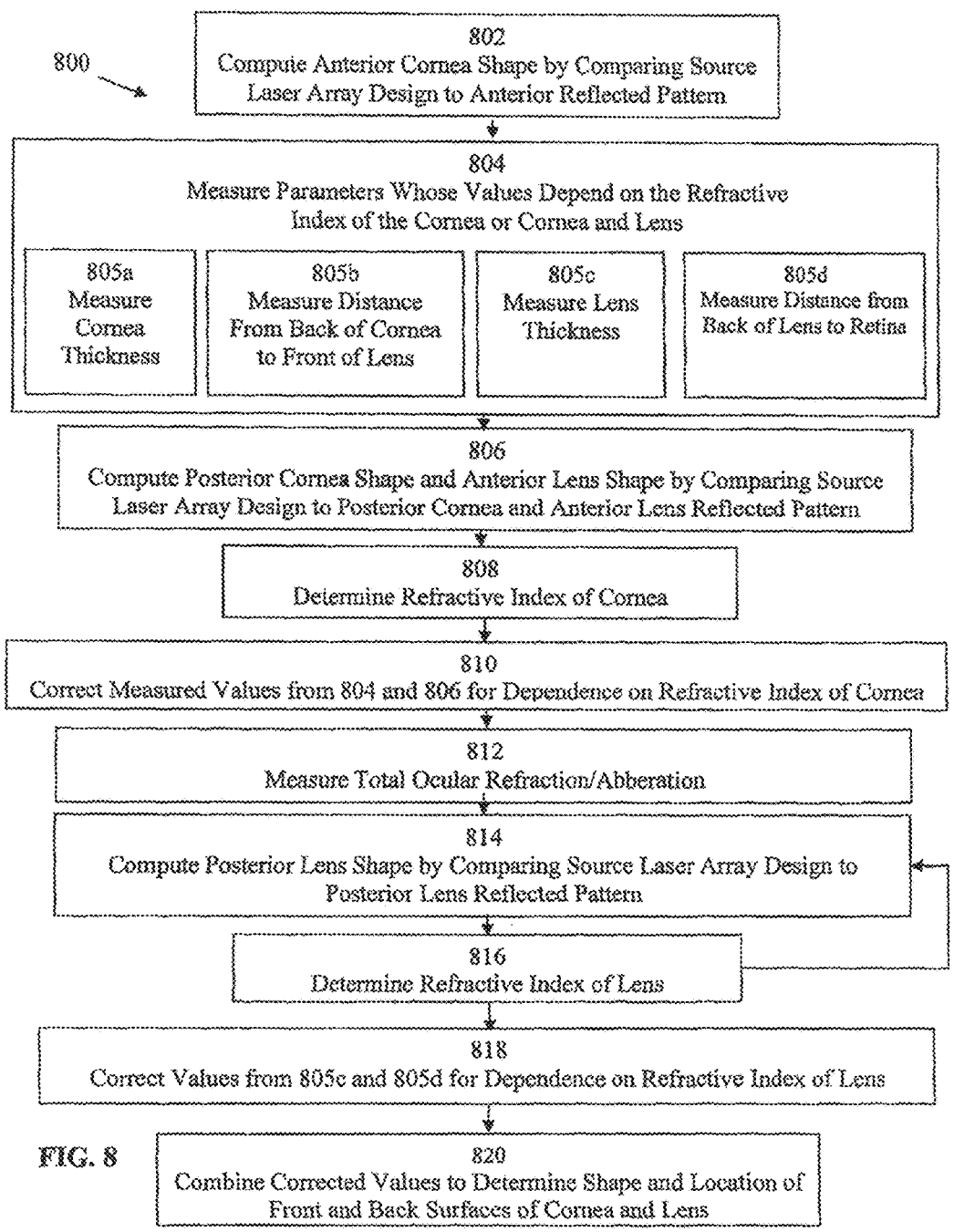
FIG. 8 illustrates one non-limiting implementation of the process of FIG. 2 to determine the shape and location of the front and back surfaces of the cornea and the front and back surfaces of the lens using the apparatus 500 of FIG. 5, according to one embodiment of the invention.
Figure 9:
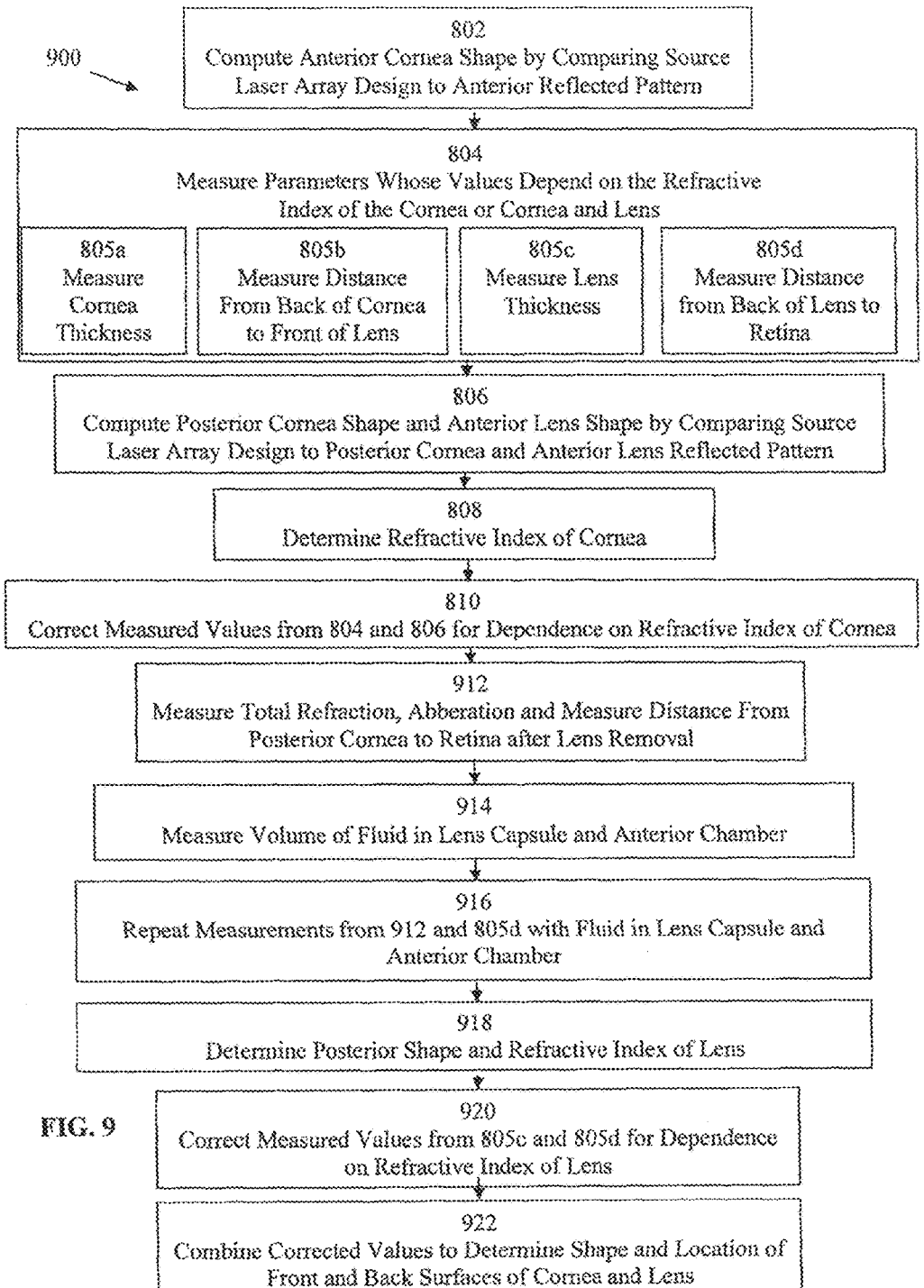
FIG. 9 illustrates an alternative non-limiting implementation of the process of FIG. 2 to determine the shape and location of the front and back surfaces of the cornea and the front and back surfaces of the lens using the apparatus 500 of FIG. 5, according to one embodiment of the invention.

It should be appreciated that the method 200 may be implemented using the apparatus 500, or other apparatus that integrate the functionality of two or more conventional measurement devices. FIGS. 8 and 9 illustrate two non-limiting implementations of the method 200 which may utilize an apparatus such as apparatus 500. FIG. 8 illustrates a method of determining the shapes and locations of the front and back surfaces of the cornea and lens at a pre-operative stage, similar to the method 300 of FIG. 3. Hence apparatus 500 may be coupled physically or by means of software to any instrument that may be used in method 200. These instruments are not limited to those using Scheimpflug, Purkinje or time-flight principles (such as topographers or optical coherence tomographers).

FIG. 9 illustrates a method of determining the shapes and locations of the front and back surfaces of the cornea and lens at an intra-operative or post-operative stage, similar to method 400 of FIG. 4.

The method 800 begins at 802 by computing the anterior cornea shape, i.e., the shape of the front surface of the cornea. This may be done by forming an averaged image from images captured by imaging devices 510a and 510b of a pattern of laser spots appearing on the front surface of the cornea. The averaged image may be compared to the known spacing and arrangement of the lasers of the laser array source (i.e., the spacing and arrangement of the lasers as they exit the laser array source). From the comparison, the shape of the front surface of the cornea may be determined.

At 804, multiple parameters whose measured values depend on the refractive index of the cornea may be measured. In the non-limiting example of FIG. 8, this includes measuring the cornea thickness (at 805a), the distance from the back surface of the cornea to the front surface of the lens (at 805b), the lens thickness (at 805c), and the distance from the back surface of the lens to the retina (at 805d). These measurements may be made using the interferometer source 508, or any other suitable instrument. These measured values may also depend on parameters other than the refractive index of the cornea. For example, the lens thickness and the distance from the back surface of the lens to the retina may also depend on the refractive index of the lens.

At 806, the posterior cornea shape (i.e., the shape of the back surface of the cornea) may be computed by comparing the known spacing and arrangement of the lasers of the laser array source to an averaged image of a pattern of laser spots appearing on the back surface of the cornea, the averaged image being an average of images of the pattern captured by imaging devices 510a and 510b. The computation may take into account any dependence the images may have on the anterior cornea shape, the cornea thickness, and the refractive index of the cornea. Also at 806, the anterior lens shape (i.e., the shape of the front surface of the lens) may be computed by comparing the known spacing and arrangement of the lasers of the laser source array to an averaged image of a pattern of laser spots appearing on the front surface of the lens. The computation may take into account any dependence of the images on the anterior cornea shape, cornea thickness, distance from the back surface of the cornea to the front surface of the lens, the posterior cornea shape, and/or the refractive index of the cornea.

At 808, the refractive index of the cornea may be determined. This may be done in any suitable manner, including using any of the methods previously described with respect to FIGS. 2-4, or any other suitable manner. According to one embodiment, the refractive index of the cornea may be determined by measuring the cornea thickness using two alternative techniques, and then reconciling the different values produced by the two techniques to determine the index of refractive. For example, the thickness of the cornea may be measured using interferometry, and may also be measured by measuring the distance visually (e.g., using a camera positioned to the side of the eye) between a spot (e.g., a laser spot) on the front of the cornea and a spot (e.g., a laser spot) on the back of the cornea. Reconciling any differences between these two values may provide the index of the refraction of the cornea. The refractive index of the cornea may depend on the wavelengths used to measure the cornea thickness (e.g., the wavelengths of the laser beams of the laser array and/or the wavelengths of the interferometer source), the anterior cornea shape, the cornea thickness, and the posterior cornea shape. Thus, the determination of the refractive index of the cornea may account for any such dependencies.

Then, at 810, the values measured at 804 and 806 may be corrected for their dependence on the corneal refractive index determined at 808, if any. One non-limiting manner for doing so is to use the techniques described in the previously cited reference to Rosales (Scheimpflug quantitative imaging of the crystalline lens and intraocular lens), although other techniques are also possible.

At 812, the total ocular refraction/aberration may be measured. This may be done in the same manner as described above with respect to FIG. 3, or in any other suitable manner.

At 814, the posterior lens shape (i.e., the shape of the back surface of the lens) may be computed by comparing the known spacing and arrangement of the lasers of the laser source array to an averaged image of a pattern of laser spots appearing on the back surface of the lens. The posterior lens shape may depend on the anterior cornea shape, the values measured at 804, the values computed at 806, the refractive index of the cornea, and/or the total ocular refraction and aberration. Thus, act 814 may account for any such dependencies.

At 816, the refractive index of the lens may be determined using a differenced image of the imaging devices 510*a* and 510*b*. This may be done in any suitable manner.

According to one embodiment, the refractive index of the lens may be determined using a single spot of the differenced image appearing on the front of the lens and the corresponding spot (e.g., from the same laser beam) appearing on the back surface of the lens. The distance between these two spots (again, from the same laser beam) may be determined using an imaging device suitably positioned at an angle to the eye. By measuring this distance, and by knowing the angle of the camera and the laser source relative to the eye, the refractive index of the lens may be calculated. Other techniques, however, may also be used. The refractive index of the lens may depend on the wavelengths of the laser array and the interferometer source, and on all of the parameters determined prior to 816. Thus, the determination at 816 may suitably combine all of the parameters to determine the refractive index of the lens.

An iteration loop comprising acts 814 and 816 may be performed any suitable number of times. However, the method 800 is not limited to performing any particular number of iterations.

At 818, the values from 805*c* and 805*d* may be corrected for their dependence on the refractive index of the lens. For example, this may be done using the techniques described in the previously cited reference to Rosales (Scheimpflug quantitative imaging of the crystalline lens and intraocular lens), or any other suitable technique. Subsequently, at 820, the shapes and locations of the front and back surfaces of the cornea and lens may be determined by suitably combining the previously determined shapes, indices of refraction, and distances/thicknesses. The act 820 may be performed by any suitable combination of hardware, software, and/or manual calculation, as the method 800 is not limited in this respect.

FIG. 9 illustrates a method of determining the shapes and locations of the front and back surfaces of the cornea and lens of an eye using apparatus 500 or a similar apparatus. The method 900 of FIG. 9 differs from method 800 in that the method 900 be performed in the context of a lens implant, thus involving removal of a patient's lens.

The method 900 is the same as method 800 for its first several acts, including acts 802-810. Thus, those acts are not described again in detail here. However, after performing act 810, method 900 continues at 912 by measuring the total ocular refraction and aberration, and the distance from the posterior cornea surface to the retina after removal of the patient's lens, which distance may depend on the refractive index of the cornea. These measurements may be made in the same manner as the measurements at act 410 of method 400, or in any other suitable manner. Alternatively, several other separate instruments described above such as those using Scheimpflug, Purkinje or time-flight principles (such as topographers or optical coherence tomographers) may also be used to measure the posterior curvature of the lens in the absence of the lens.

After removal of the patient's lens, fluid may be inserted into the lens capsule and/or anterior chamber, as previously described with respect to FIG. 4. In some embodiments, the fluid may have a known refractive index. At 914, the volume of fluid in the lens capsule and anterior chamber may be measured using any suitable technique (e.g., a graduated syringe, or any other suitable technique).

At 916, the measurements from 912 and 905*d* may be repeated with the fluid in the lens capsule and anterior chamber. These measured values may depend on the refractive index of the cornea, the values measured at 612, and the refractive index of the fluid. Thus, values measured at 916 may be corrected for their dependence, if any, on the refractive index of the cornea, the values measured at 612, and the refractive index of the fluid.

At 918, the posterior lens shape and refractive index of the lens may be determined. This determination may performed in any suitable manner. For example, the posterior lens shape may be determined from an averaged image of multiple imaging devices of a pattern of laser spots appearing on the posterior lens, as previously described.

The refractive index may be determined from a differenced image of the pattern of laser spots. The measured values for each of the posterior lens shape and lens refractive index may be corrected for their dependence on the other values measured and determined in method 900. For example, the refractive index of the lens may be corrected for all of the previously measured values in method 900 and the wavelengths used to measure the cornea thickness (e.g., the wavelengths of any one or more optical methods used for measuring the cornea thickness), according to one non-limiting embodiment. The measured posterior lens shape may be corrected for its dependence on the refractive index of the fluid inserted into the lens capsule and anterior chamber, the refractive index of the lens, and all of the values from 802-916.

It should be appreciated that 918 may included one or more iterations within the act. For example, the determined posterior lens shape may depend on the refractive index of the lens, and vice versa. Therefore, one or more iterations may be performed in determining these values. At 920, the measured values from 805*c* and 805*d* may be corrected for their dependence on the refractive index of the lens, if any, in any suitable manner.

At 922, the values may be combined to model the shapes and locations of the front and back surfaces of the cornea and lens. These combinations may be performed using a processor (e.g., processor 516), or any other suitable device. The combinations may involve utilizing ray tracing software in some embodiments.

It should be appreciated that the various methods and apparatus described herein may be used for various applications. For example, ray tracing may be used to accurately predict and analyze the operation of ocular components when ocular parameters, such as shapes, indices of refraction, and distances are accurately known. Thus, according to some aspects, accurate determination of the indices of refraction, shapes, and ocular distances described above may enable use of ray tracing techniques to analyze the behavior of the ocular structure. Such techniques may avoid any reliance on historical averages of ocular parameters, such as historical averages of indices of refraction. Rather, the techniques described herein may be used to accurately determine ocular parameters for a given patient, allowing accurate application of ray tracing analysis to that particular patient's eye.

In addition, the technology described herein may facilitate calculation of the dimensions (i.e., power) of an intraocular lens implant (e.g., for replacing a cloudy lens (cataract) in eyes that had previous laser corrective surgery, or for any other reason), and thus may facilitate design of customized intraocular lenses. The optical effects of the intraocular lens implant may also be accurately predicted prior to surgery and analyzed after surgery. For example, the techniques described herein may facilitate determination of the kinetics of natural or implanted intraocular lenses based on changes in optics as the lenses move within an eye. Thus, for example, optical changes resulting from post-operative wound healing may be calculated. Moreover, according to some aspects, neural networks (e.g., a computer network that learns from prior data) may be used to compile databases of average intraocular kinetics and optical changes from wound healing.

Moreover, the techniques described herein may be used to provide improved accuracy of all types of ophthalmic devices, for example by facilitating correction of the such devices for their dependency (if any) on the varying refractive index of an individual's eye.

In addition, the various techniques described herein may facilitate accurate determination of pupil size. For example, pupil size may be measured and then accurate values of corneal topography and the corneal refractive index, determined by any of the techniques previously described, may be used to correct the measured pupil size to produce a more accurate determination of pupil size. Accurately knowing the pupil size may facilitate ocular modeling (e.g., only rays entering the pupil may be considered in some embodiments), modeling of diffraction, simulating vision, calculating aberration, etc.

As has been described, ray tracing software may be used in various embodiments, and may facilitate prediction and analysis of optical behavior within the eye. For example, simulations of the optical behavior within the eye may be performed and represented visually on a display screen (e.g., a computer screen) in the form of reduced Snellen/Landolt C/ETDRS vision or pictures. Other forms of visual representation are also possible. Surgeons may use such visuals to analyze optical behavior, and the visuals may assist in selection of an appropriate surgery (e.g., presbyopic LASIK, concutive keratoplasty, etc.) and/or an appropriate implant (e.g., bifocal intraocular lens, etc.). According to some embodiments, the ray tracing software may be used to simulate wavefront refraction and wavefront aberration of an eye prior to surgery.

According to one aspect, ray tracing may be used to determine differences in the index of the refraction with the cornea and/or lens. For example, the lens may be made up of zones of differing density (known as gradient index, or "GRIN"), which may be accurately modeled ray tracing. The techniques described herein may utilize composite indices of refraction of the cornea and lens in some embodiments, but in other embodiments may use indices of refraction that vary within these structures.

According to one aspect of the technology described herein, a method for determining the effective position of a lens is provided. Natural lenses and lens implants often differ in shape.

When performing a lens replacement, it may be desirable to position the lens implant substantially at the same location as that at which the natural lens was positioned. Because the shapes of the natural lens and lens implant may differ, it may be difficult to position the front and back surfaces of the implant at the same locations at which the front and back surfaces of the natural lens were positioned within the eye. Thus, according to one aspect, an "effective position" of the natural lens may be determined, and may be used as the desired placement of the lens implant. An example is described with respect to FIG. 10.

Figure 10:
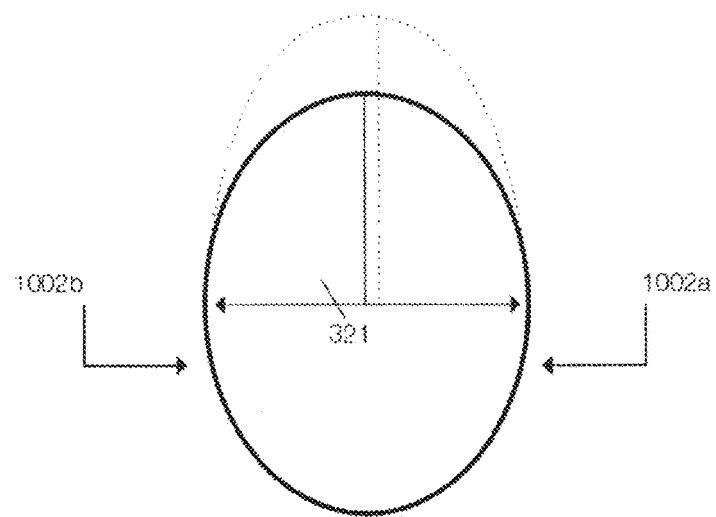
FIG. 10 illustrates various locations within a lens which may be determined to be an "effective location" of the lens, according to one embodiment of the invention.

FIG. 10 illustrates a non-limiting example of a cross-section of a natural lens. The lens has an anterior surface 1002a and a posterior surface 1002b. If the lens is to be removed during lens replacement surgery, it may be desirable to know where to position the replacement lens, which may not take the shape shown in FIG. 10. Various methods of determining an "effective position" of the lens may be used. For example, according to one embodiment, the effective lens position is calculated using the position of the lens as determined by interferometry in an un-dilated pupil state.

According to another embodiment, the "effective position" of the lens may be determined by extrapolating the topographies of the anterior and posterior lens surfaces 1002a and 1002b. The point at which these two topographies meet may be considered a presumptive equator of the lens, and the ratio of the that point to the apex of the anterior and poster lens surfaces may be used as the effective lens position, shown as point 1 in FIG. 10.

According to another embodiment, the effective lens position may be determined by first obtaining a diameter of the lens in any suitable manner (e.g., using ultrasound, using the volume of fluid inserted into the lens capsule, or any other suitable manner), and then extrapolating the anterior and posterior lens surfaces to the diameter. The midpoint of the arc length of the lens may then be used as the effective lens position, shown as point 2 in FIG. 10.

According to another embodiment, simulated topography of the posterior lens surface may be used to determine the effective position of the lens. The simulated posterior topography may be obtained by approximating a best-fit curve for posterior topography using anterior lens topography, lens thickness, and a historical ratio between the anterior and posterior lens curvatures. The resulting effective lens position may be represented by point 3 in FIG. 10. Once the effective location of the lens is determined (whether being point 1, point 2, or point 3), a replacement lens may be positioned at substantially the same location.

Regression analysis of any of the previously described method for determining the effective location of the lens may be used to increase accuracy of the results. Also, one or more of the techniques described previously herein may be used to facilitate the determination of effective lens position. For example, low/partial coherence interferometry may be performed after removal of the natural lens to obtain distances in the absence of the lens.

Ray tracing may be used to determine shapes, indices of refraction, and/or distances in the absence of the lens. Pre-operative and intra-operative measurements of topography and interferometry may be used to increase accuracy of measurements and calculated positions, for example by providing additional information for use in iteration loops of any of the methods described above.

According to one embodiment, stretch or elasticity coefficients may be determined, and may facilitate lens design and/or determining the location of lens implants.

For example, lens capsule elasticity may be used to predict the final positioning of a lens after insertion in into the lens capsule. The elasticity coefficients may be determined using lens dimension data, patient age, and thickness of the lens capsule, among other considerations. Elasticity of a lens implant may similarly be considered.

It should be appreciated that various techniques described herein may therefore be used to design lenses, for example including lens implants. The techniques may apply to designing various types of lenses, including, but not limited to, plano, convex, concave, multifocal (refractive, diffractive, etc.), toric, accommodative, prismatic, multiple lens configurations, variable curvature (e.g., aspherical), phakic intraocular lenses, light adjustable lenses, or any combination of those listed.

Additionally, one or more of the techniques described herein may be used in the context of planning or performing various types of surgeries. Such surgeries may include, but are not limited to, cornea/refractive surgery, lens surgery and retinal surgery. Various types of refractive surgery may include, but are not limited to, myopic, hyperopic and presbyopic LASIK, LASEK, or PRK, conductive keratoplasty, radial keratotomy or a combination of the above.

It should be appreciated that the various aspects described above are not limited to human eyes, but rather may be applied to any type of eye, including human eyes or any other animals. In addition, while various aspects have been described as relating to structures of the eye and implants for the eye, it should be appreciated that the techniques may also apply to additional elements, such as glasses, contact lenses, or other elements used for ocular purposes As previously mentioned, it should be appreciated that the methods and apparatus described above may be used to form a model of any number of structures of interest within an eye. For example, according to some embodiments, a complete model of the eye may be formed. In other embodiments, a model of a single structure (e.g., the lens, or a surface of the lens) may be formed. In still other embodiments, the methods and/or apparatus described above may be used to determine a single parameter of interest of a structure.

Thus, individual acts of the methods described above may be used for some applications, irrespective of whether the other acts are also performed.

The above-described embodiments of the present technology can be implemented in any of numerous ways. For example, the embodiments may be implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be generically considered as one or more controllers that control the above-discussed functions. The one or more controllers can be implemented in numerous ways, such as with dedicated hardware, or with general purpose hardware (e.g., one or more processors) that is programmed using microcode or software to perform the functions recited above. In this respect, it should be appreciated that one implementation of the embodiments of the present technology comprises at least one computer-readable storage medium (e.g., a computer memory, a floppy disk, a compact disk, a tape, a flash drive, etc.) encoded with a computer program (i.e., a plurality of instructions), which, when executed on a processor, performs the above-discussed functions of the embodiments of the present technology. The computer-readable storage medium can be transportable such that the program stored thereon can be loaded onto any computer resource to implement the aspects of the present technology discussed herein. In addition, it should be appreciated that the reference to a computer program which, when executed, performs the above-discussed functions, is not limited to an application program running on a host computer. Rather, the term computer program is used herein in a generic sense to reference any type of computer code (e.g., software or microcode) that can be employed to program a processor to implement the above-discussed aspects of the technology.

While various inventive embodiments have been described and illustrated herein, those of ordinary skill in the art will readily envision a variety of other means and/or structure for performing the function and/or obtaining the results and/or one or more of the advantages described herein, and each of such variations and/or modifications is deemed to be within the scope of the inventive embodiments described herein. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present technology are directed to each individual feature, system, article, material, kit, and/or method described herein. In addition, any combination of two or more such features, systems, articles, materials, kits, and/or methods, if such features, systems, articles, materials, kits, and/or methods are not mutually inconsistence, is included within the inventive scope of the present disclosure. All definitions, as defined and used herein, should be understood to control over dictionary definitions, definitions in documents incorporated by reference, and/or ordinary meanings of the defined terms. The indefinite articles "a" and "an," as used herein in the specification and in the claims, unless clearly indicated to the contrary, should be understood to mean "at least one." The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternative (i.e., "one or the other but not both") when preceded by terms of exclusivity, such as "either," "one of," "only one of," or "exactly one of" "Consisting essentially of," when used in the claims, shall have its ordinary meaning as used in the field of patent law. As used herein the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a nonlimiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than, B (and optionally including other elements); etc. It should also be understood that, unless clearly indicated to the contrary, in any methods claimed herein that include more than one step or act, the order of the steps or acts of the method is not necessarily limited to the order in which the steps or acts of the method are recited. In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The words "comprises/comprising" and the words "having/including" when used herein with reference to the present invention are used to specify the presence of stated features, integers, steps or components but does not preclude the presence or addition of one or more other features, integers, steps, components or groups thereof. It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

What is claimed is:

1. A method of modelling an eye, the method comprising:
computing an anterior shape of an anterior surface of a cornea of the eye by comparing a source laser array to an anterior reflected cornea pattern;
measuring eye parameters including: a corneal thickness, an anterior chamber depth, a lens thickness, and an axial length of the eye;
computing a posterior shape of a posterior surface of the cornea of the eye by comparing the source laser array to a posterior reflected cornea pattern;
determining a refractive index of the cornea;
correcting the measured eye parameters to account for the effect of the refractive index of the cornea on the measured eye parameters;
measuring a total aberration or a total refraction of the eye;
determining a refractive index of the lens;
further correcting the measured eye parameters to account for the effect of the refractive index of the lens on the measured eye parameters; and
combining the further corrected eye parameters to determine a shape and location of the anterior and posterior surfaces of the cornea and the anterior and posterior surfaces of the lens.

2. The method of claim 1 wherein the eye parameter measurements are made using topography or interferometery.

3. The method of claim 1 wherein the refractive index of the cornea is determined using a refractometer or an aberrometer.

4. The method of claim 1 wherein the refractive index of the cornea is determined by the corneal thickness, the computed anterior shape and the computed posterior shape.

5. The method of claim 1 wherein the aberration of the eye is measured using a refractometer or an aberrometer.

6. The method of claim 1 wherein the refractive index of the lens is determined by computing a posterior lens shape, the posterior lens shape determined by comparing the source laser array to a posterior reflected lens pattern.

7. The method of claim 6 wherein computing the posterior lens shape comprises:
capturing one or more images of the posterior reflected cornea pattern;
forming an averaged image from the captured images; and
comparing the averaged image to spacing and arrangement of the lasers of the source laser array.

8. The method of claim 1 wherein the refractive index of the lens is determined by computing an anterior lens shape, the anterior lens shape determined by comparing the source laser array to an anterior reflected lens pattern.

9. The method of claim 8 wherein computing the anterior lens shape comprises:
capturing one or more images of the anterior reflected lens pattern;
forming an averaged image from the captured images; and
comparing the averaged image to spacing and arrangement of the lasers of the source laser array.

10. The method of claim 1 wherein further comprising: measuring a volume of aqueous in the eye.

11. The method of claim 1 wherein computing the anterior shape of the cornea further comprises:
capturing one or more images of the anterior reflected cornea pattern;
forming an averaged image from the captured images; and
comparing the averaged image to spacing and arrangement of the lasers of the source laser array.

12. The method of claim 1 wherein computing the posterior shape of the cornea of the eye comprises:
capturing one or more images of the posterior reflected cornea pattern;
forming an averaged image from the captured images; and
comparing the averaged image to spacing and arrangement of the lasers of the source laser array.

13. The method of claim 1 wherein the refractive index of the lens is determined using a difference image determined using the reflection of one laser spot appearing on the anterior of the lens and the corresponding spot appearing on the posterior of the lens.

14. A method of determining an optimum position for a replacement intraocular lens based on the effective position of the natural lens, the natural lens having an anterior surface and a posterior surface, the method comprising:

modelling the anterior and posterior surfaces of the natural lens using the method of claim 1;

extrapolating the anterior and posterior surfaces to cross points; and determining the optimum position to line in the place joining said cross points.

15. A method of determining an optimum position for a replacement intraocular lens based on the effective position of the natural lens, the natural lens having an anterior surface and a posterior surface, the method comprising:

modelling the anterior and posterior surfaces of the natural lens using the method of claim 1;

determining the diameter of the natural lens;

extrapolating the anterior and posterior lens surfaces to the diameter;

determining the arc length of the natural lens using said diameter; and determining the optimum position to lie at the midpoint of the arc length.

16. A method of determining an optimum position for a replacement intraocular lens based on the effective position of the natural lens, said natural lens having an anterior surface and a posterior surface; the method comprising:

modelling the anterior and posterior surfaces of the natural lens using the method claim 1; and approximating a best fit curve for the posterior surface using the anterior lens surface, lens thickness and a historical ratio between the anterior and posterior lens curvatures.

* * * * *